United States Patent
Kilcoin et al.

(10) Patent No.: US 11,771,462 B2
(45) Date of Patent: Oct. 3, 2023

(54) STERNAL LOCATORS AND ASSOCIATED SYSTEMS AND METHODS

(71) Applicant: TELEFLEX LIFE SCIENCES LIMITED, Valletta (MT)

(72) Inventors: Christopher Brian Kilcoin, Santa Cruz, CA (US); John Frank Morgan, III, San Antonio, TX (US); Larry J. Miller, Spring Branch, TX (US); Robert W. Titkemeyer, San Antonio, TX (US)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 444 days.

(21) Appl. No.: 15/643,707

(22) Filed: Jul. 7, 2017

(65) Prior Publication Data

US 2017/0303963 A1 Oct. 26, 2017

Related U.S. Application Data

(62) Division of application No. 13/546,894, filed on Jul. 11, 2012, now Pat. No. 9,730,729.

(Continued)

(51) Int. Cl.
*A61B 17/34* (2006.01)
*A61B 17/16* (2006.01)
(Continued)

(52) U.S. Cl.
CPC ...... *A61B 17/3472* (2013.01); *A61B 17/1637* (2013.01); *A61B 17/17* (2013.01);
(Continued)

(58) Field of Classification Search
CPC ............. A61M 5/158; A61M 5/3286; A61M 2005/14252; A61M 2005/1587; A61M 39/0247; A61M 2039/025; A61M 2039/0258; A61M 2039/0261; A61M 2039/0273; A61M 2039/0276; A61B 17/3472; A61B 10/025; A61B 2010/0258; A61B 2017/1789; A61B 17/3043; A61B 2018/3405; A61B 2017/3407; A61B 17/823; A61B 17/3494; A61B 17/1637;
(Continued)

(56) References Cited

U.S. PATENT DOCUMENTS

| | | |
|---|---|---|
| 2,001,638 A | 5/1935 | Tornsjo |
| 2,317,648 A | 4/1943 | Siqveland |

(Continued)

FOREIGN PATENT DOCUMENTS

| | | |
|---|---|---|
| CA | 2138842 A1 | 6/1996 |
| CA | 2454600 A1 | 2/2003 |

(Continued)

OTHER PUBLICATIONS

International Preliminary Report on Patentability in PCT Application No. PCT/US2012/046294, dated Jan. 23, 2014.

(Continued)

*Primary Examiner* — Scott J Medway
(74) *Attorney, Agent, or Firm* — BakerHostetler

(57) ABSTRACT

Apparatuses, systems, and methods for sternal locators for placement of an intraosseous device into the sternum of a human patient.

20 Claims, 28 Drawing Sheets

Related U.S. Application Data

(60) Provisional application No. 61/506,316, filed on Jul. 11, 2011.

(51) Int. Cl.
*A61B 17/17* (2006.01)
*A61B 10/02* (2006.01)

(52) U.S. Cl.
CPC .. *A61B 17/3494* (2013.01); *A61B 2010/0258* (2013.01); *A61B 2017/3407* (2013.01); *A61B 2017/3492* (2013.01); *F04C 2270/0421* (2013.01)

(58) Field of Classification Search
CPC .. A61B 17/17; A61B 17/1691; A61B 17/1693
See application file for complete search history.

(56) References Cited

U.S. PATENT DOCUMENTS

| | | | |
|---|---|---|---|
| 3,815,605 A * | 6/1974 | Schmidt | A61B 17/1604 606/182 |
| 3,991,765 A | 11/1976 | Cohen | |
| 4,142,517 A | 3/1979 | Stavropoulos et al. | |
| 4,170,993 A | 10/1979 | Alvarez | |
| 4,646,731 A | 3/1987 | Brower | |
| 4,659,329 A | 4/1987 | Annis | |
| 4,758,225 A | 7/1988 | Cox et al. | |
| 4,772,261 A | 9/1988 | Von Hoff et al. | |
| 4,969,870 A | 11/1990 | Kramer et al. | |
| 5,057,085 A | 10/1991 | Kopans | |
| 5,116,324 A | 5/1992 | Brierley et al. | |
| 5,120,312 A | 6/1992 | Wigness et al. | |
| 5,122,114 A | 6/1992 | Miller et al. | |
| 5,195,985 A | 3/1993 | Hall | |
| 5,203,056 A | 4/1993 | Funk et al. | |
| 5,312,364 A * | 5/1994 | Jacobs | A61B 17/3472 604/174 |
| 5,332,398 A | 7/1994 | Miller et al. | |
| 5,372,583 A | 12/1994 | Roberts et al. | |
| 5,385,553 A | 1/1995 | Hart et al. | |
| 5,423,824 A | 6/1995 | Akerfeldt et al. | |
| 5,431,655 A | 7/1995 | Melker et al. | |
| 5,451,210 A | 9/1995 | Kramer et al. | |
| 5,484,442 A | 1/1996 | Melker et al. | |
| 5,591,188 A | 1/1997 | Waisman | |
| 5,601,559 A | 2/1997 | Melker et al. | |
| 5,733,262 A | 3/1998 | Paul | |
| 5,769,086 A | 6/1998 | Ritchart et al. | |
| 5,779,708 A | 7/1998 | Wu | |
| 5,817,052 A | 10/1998 | Johnson et al. | |
| 5,858,005 A | 1/1999 | Kriesel | |
| 5,868,711 A | 2/1999 | Kramer et al. | |
| 5,960,797 A | 10/1999 | Kramer et al. | |
| 6,018,094 A | 1/2000 | Fox | |
| 6,228,088 B1 | 5/2001 | Miller et al. | |
| 6,458,117 B1 * | 10/2002 | Pollins, Sr. | A61B 17/3472 604/164.01 |
| 6,761,726 B1 * | 7/2004 | Findlay | A61B 10/025 604/506 |
| 7,008,383 B1 | 3/2006 | Damadian et al. | |
| 7,137,985 B2 | 11/2006 | Jahng | |
| 7,207,949 B2 | 4/2007 | Miles et al. | |
| 7,347,840 B2 * | 3/2008 | Findlay | A61B 10/025 604/180 |
| 7,481,830 B2 | 1/2009 | Wall et al. | |
| 7,615,043 B2 | 11/2009 | Zhou | |
| 7,670,328 B2 | 3/2010 | Miller | |
| 7,699,850 B2 | 4/2010 | Miller | |
| 7,811,260 B2 * | 10/2010 | Miller | A61B 17/3476 604/188 |
| 7,815,642 B2 | 10/2010 | Miller | |
| 7,850,620 B2 | 12/2010 | Miller et al. | |
| 7,899,528 B2 | 3/2011 | Miller et al. | |
| 7,951,089 B2 | 5/2011 | Miller | |
| 8,038,664 B2 | 10/2011 | Miller et al. | |
| 8,142,365 B2 * | 3/2012 | Miller | A61B 17/32002 600/566 |
| 8,217,561 B2 | 7/2012 | Fukuzawa et al. | |
| 8,308,693 B2 | 11/2012 | Miller et al. | |
| 8,333,769 B2 * | 12/2012 | Browne | A61B 17/3472 606/86 R |
| 8,419,683 B2 | 4/2013 | Miller et al. | |
| 8,480,632 B2 | 7/2013 | Miller et al. | |
| 8,486,027 B2 | 7/2013 | Findlay et al. | |
| 8,506,568 B2 | 8/2013 | Miller | |
| 8,641,715 B2 | 2/2014 | Miller | |
| 8,656,929 B2 | 2/2014 | Miller et al. | |
| 8,668,698 B2 | 3/2014 | Miller et al. | |
| 8,684,978 B2 | 4/2014 | Miller et al. | |
| 8,690,791 B2 | 4/2014 | Miller | |
| 8,715,287 B2 | 5/2014 | Miller | |
| 8,812,101 B2 | 8/2014 | Miller et al. | |
| 8,870,872 B2 | 10/2014 | Miller | |
| 8,876,826 B2 | 11/2014 | Miller | |
| 8,944,069 B2 | 2/2015 | Miller et al. | |
| 8,974,410 B2 | 3/2015 | Miller et al. | |
| 8,998,848 B2 | 4/2015 | Miller et al. | |
| 9,072,543 B2 | 7/2015 | Miller et al. | |
| 9,078,637 B2 | 7/2015 | Miller | |
| 9,439,667 B2 * | 9/2016 | Miller | A61B 17/1637 |
| 9,839,740 B2 * | 12/2017 | Beamer | A61M 5/00 |
| 2003/0225344 A1 | 12/2003 | Miller | |
| 2003/0225411 A1 | 12/2003 | Miller | |
| 2004/0064136 A1 | 4/2004 | Papineau et al. | |
| 2004/0215102 A1 | 10/2004 | Ikehara et al. | |
| 2004/0220497 A1 | 11/2004 | Findlay et al. | |
| 2005/0027210 A1 | 2/2005 | Miller | |
| 2005/0040060 A1 | 2/2005 | Andersen et al. | |
| 2005/0131345 A1 | 6/2005 | Miller | |
| 2005/0148940 A1 | 7/2005 | Miller | |
| 2005/0165403 A1 | 7/2005 | Miller | |
| 2005/0165404 A1 | 7/2005 | Miller | |
| 2005/0171504 A1 | 8/2005 | Miller | |
| 2005/0182420 A1 | 8/2005 | Schulte et al. | |
| 2005/0228309 A1 | 10/2005 | Fisher et al. | |
| 2005/0261693 A1 | 11/2005 | Miller et al. | |
| 2005/0273076 A1 * | 12/2005 | Beasley | A61M 25/007 604/526 |
| 2006/0030815 A1 * | 2/2006 | Csincsura | A61M 5/158 604/93.01 |
| 2006/0036212 A1 | 2/2006 | Miller | |
| 2006/0052790 A1 | 3/2006 | Miller | |
| 2006/0167378 A1 | 7/2006 | Miller | |
| 2006/0167379 A1 | 7/2006 | Miller | |
| 2006/0184063 A1 | 8/2006 | Miller | |
| 2007/0016100 A1 | 1/2007 | Miller | |
| 2007/0049945 A1 | 3/2007 | Miller | |
| 2007/0149920 A1 | 6/2007 | Michels et al. | |
| 2007/0270775 A1 | 11/2007 | Miller et al. | |
| 2008/0045857 A1 | 2/2008 | Miller et al. | |
| 2008/0045861 A1 | 2/2008 | Miller et al. | |
| 2008/0045965 A1 | 2/2008 | Miller et al. | |
| 2008/0071215 A1 * | 3/2008 | Woods | A61B 17/3403 604/116 |
| 2008/0140014 A1 | 6/2008 | Miller et al. | |
| 2008/0208136 A1 | 8/2008 | Findlay et al. | |
| 2008/0215056 A1 | 9/2008 | Miller et al. | |
| 2008/0221580 A1 | 9/2008 | Miller et al. | |
| 2009/0204024 A1 * | 8/2009 | Miller | A61B 17/3472 600/567 |
| 2010/0004626 A1 * | 1/2010 | Miller | A61B 10/025 604/506 |
| 2010/0152616 A1 | 6/2010 | Beyhan et al. | |
| 2010/0298784 A1 | 11/2010 | Miller | |
| 2010/0298831 A1 * | 11/2010 | Browne | A61B 17/1615 606/79 |

(56) References Cited

U.S. PATENT DOCUMENTS

| | | | |
|---|---|---|---|
| 2010/0312246 A1 | 12/2010 | Browne et al. | |
| 2013/0041345 A1* | 2/2013 | Kilcoin | A61B 17/17 604/506 |

FOREIGN PATENT DOCUMENTS

| | | | |
|---|---|---|---|
| CN | 2664675 Y | 12/2004 | |
| CN | 1913833 A | 2/2007 | |
| CN | 101325914 A | 12/2008 | |
| CN | 101325984 A | 12/2008 | |
| CN | 101360526 A | 2/2009 | |
| CN | 101541370 A | 9/2009 | |
| EP | 0984809 B1 | 8/2005 | |
| FR | 853349 A | 3/1940 | |
| FR | 2457105 A1 | 12/1980 | |
| JP | H06-508773 A | 10/1994 | |
| JP | H07-171165 A | 7/1995 | |
| WO | 9806337 | 2/1998 | |
| WO | 1998006337 A1 | 2/1998 | |
| WO | 0193931 | 12/2001 | |
| WO | 2002096497 A1 | 12/2002 | |
| WO | 2005112800 A2 | 12/2005 | |
| WO | 2008016757 A2 | 2/2008 | |
| WO | 2008054894 A2 | 5/2008 | |
| WO | 2008081438 | 7/2008 | |
| WO | 2009070896 | 6/2009 | |
| WO | 2010020606 A1 | 2/2010 | |
| WO | 2011070593 | 6/2011 | |
| WO | 2011070593 A1 | 6/2011 | |
| WO | WO-2011070593 A1 * | 6/2011 | A61B 17/3472 |
| WO | 2013009901 A2 | 1/2013 | |

OTHER PUBLICATIONS

Notice of Allowance in U.S. Appl. No. 11/380,340 dated Aug. 22, 2014.
Notice of Allowance in U.S. Appl. No. 14/721,144 dated Jul. 22, 2014.
Notice of Allowance in U.S. Appl. No. 11/619,390 dated Jul. 3, 2014.
Notice of Allowance in U.S. Appl. No. 11/619,390 dated Nov. 6, 2014.
Notice of Allowance in U.S. Appl. No. 12/259,745 dated Nov. 7, 2014.
Extended European Search Report in EP Application No. 12811090. 5, dated Jan. 21, 2015.
Notice of Allowance in U.S. Appl. No. 12/718,638, dated Aug. 3, 2015.
Notice of Allowance in U.S. Appl. No. 13/966,104, dated Aug. 17, 2015.
"Proven reliability for quality bone marrow samples," Special Procedures, Cardinal Health, 6 pages (2003).
Vidacare Corporation, Comments to Intraosseous Vascular Access Position Paper, Infusion Nurses Society, 6 pages (May 4, 2009).
Astrom, K. G., "CT-guided Transsternal Core Biopsy of Anterior Mediastinal Masses," Radiology 1996; 199:564-567 (May 1996).
Astrom, K. G., "Automatic Biopsy Instruments Used Through a Coaxial Bone Biopsy System with an Eccentric Drill Tip," Acta Radiological, 1995; 36:237-242 (May 1995).
BioAccess.com, "Single Use Small Bone Power Tool—How it Works," 1 pg (Jun. 9, 2008).
Buckley et al., "CT-guided bone biopsy: Initial experience with commercially available handheld Black and Decker drill," European Journal of Radiology 61, pp. 176-180 (2007).
Cummins, Richard O., et al, "ACLS—Principles and Practice," ACLS—The Reference Textbook, American Heart Association, pp. 214-218 (2003).
F.A.S.T. 1 Intraosseous Infusion System with Depth-Control Mechanism Brochure, 6 pages (2000).
Gunal et al., "Compartment Syndrome After Intraosseous Infusion: An Experimental Study in Dogs," Journal of Pediatric Surgery, vol. 31, No. 11, pp. 1491-1493 (Nov. 1996).
Hakan et al., "CT-guided Bone Biopsy Performed by Means of Coaxial Biopsy System with an Eccentric Drill," Radiology, pp. 549-552 (Aug. 1993).
Liakat A. Parapia, "Trepanning or trephines: a history of bone marrow biopsy," British Journal of Haematology, pp. 14-19 (2007).
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark," The Wall Street Journal, Factiva, 5 pages (2008).
Riley et al., "A Pathologists Perspective on Bone Marrow Aspiration Biopsy: I. Performing a Bone Marrow Examination," Journal of Clinical Laboratory Analysis 18, pp. 70-90 (2004).
Pediatrics, "2005 American Heart Association Guidelines for Cardiopulmonary Resuscitation and Emergency Cardiovascular Care of Pediatric and Neonatal Patients: Pediatric Advanced Life Support," www.pediatrics.org, Official Journal of the American Academy of Pediatrics, 26 pages (Feb. 21, 2007).
Office Communication for European Patent Application No. 03756317. 8, dated Oct. 2, 2007.
Office Communication for Chinese Patent Application No. 201280043008.5, dated Jan. 15, 2016.
European Search Report for European Patent Application No. 03756317.8, dated Jan. 21, 2015.
Notice of Reasons for Rejection for Japanese Patent Application No. 2014-520284, dated May 30, 2016.
Office Communication for Russian Patent Application No. 2014104585, dated Jun. 14, 2016.
Notice of Allowance in U.S. Appl. No. 13/546,894 dated Apr. 10, 2017.

* cited by examiner

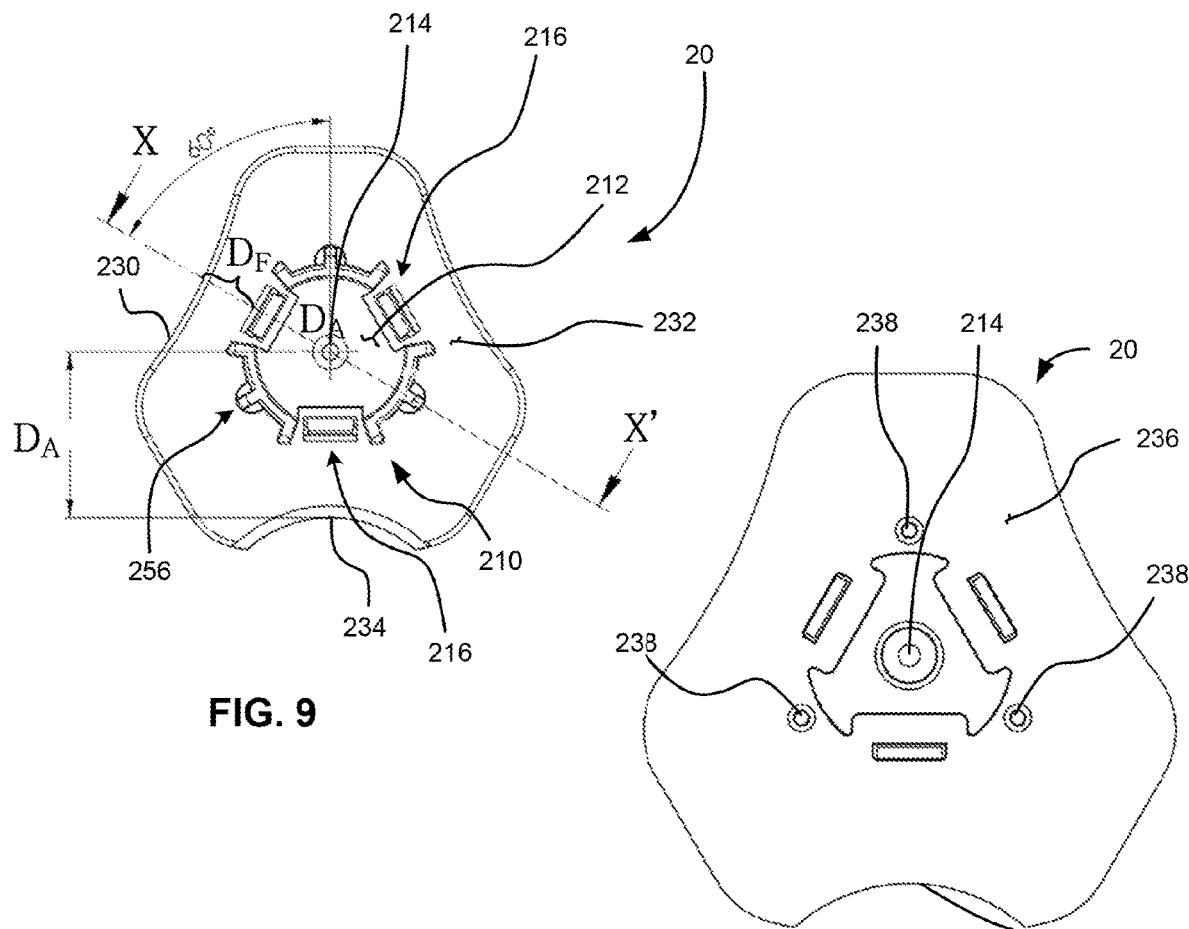
FIG. 9
FIG. 10
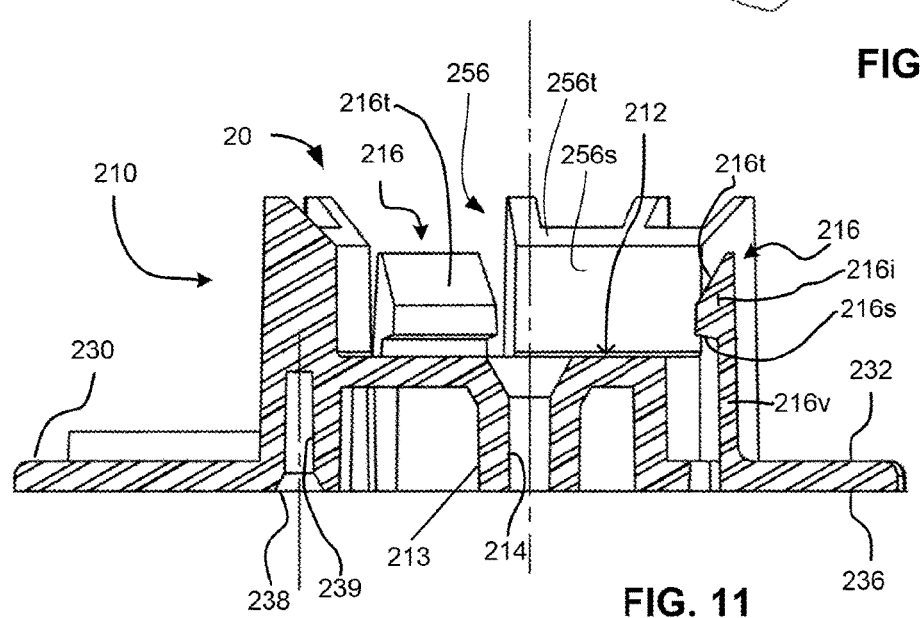
FIG. 11

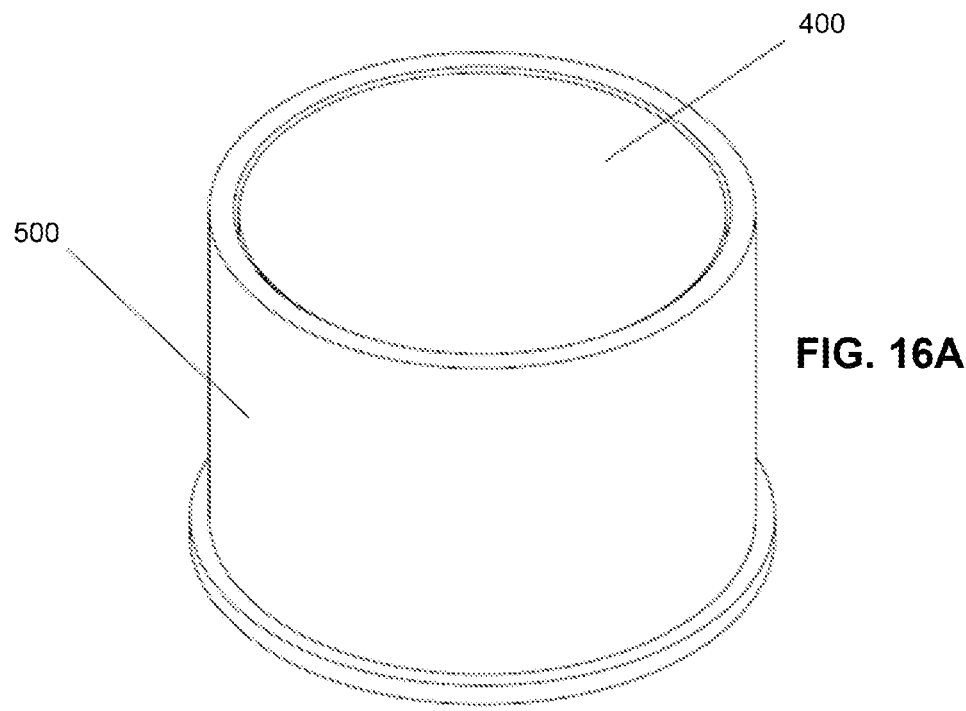
FIG. 16A
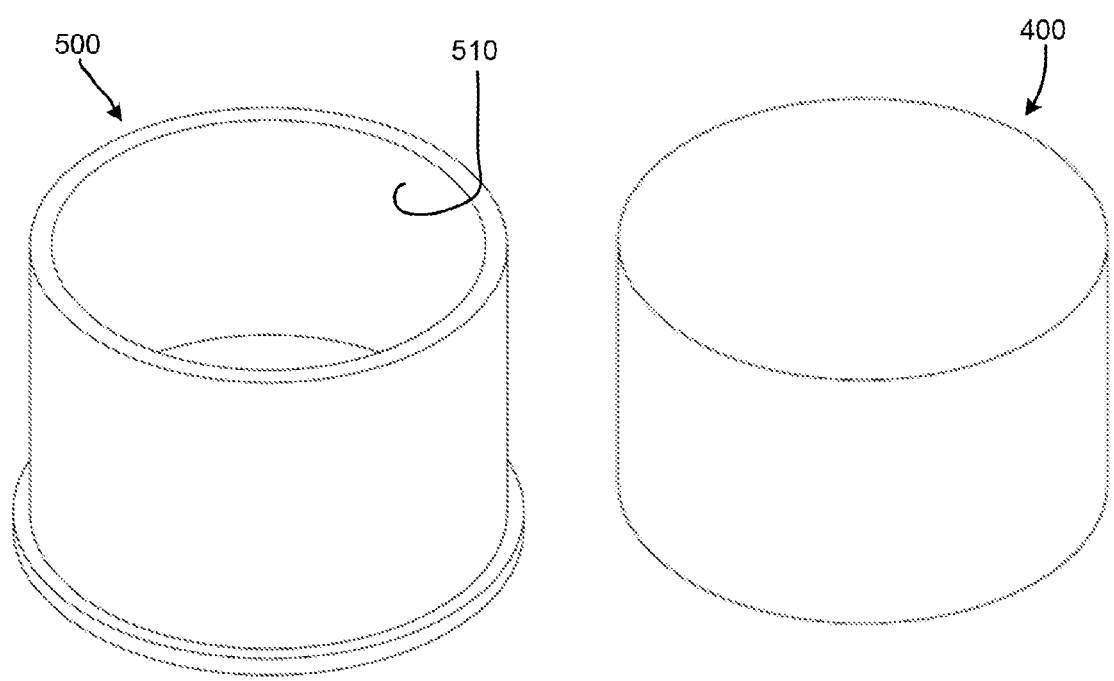
FIG. 16B
FIG. 16C

STERNAL LOCATORS AND ASSOCIATED SYSTEMS AND METHODS

CROSS-REFERENCE TO RELATED APPLICATIONS

This application is a divisional application of U.S. patent application Ser. No. 13/546,894, filed Jul. 11, 2012, and published as U.S. Patent Application Publication No. 2013/0041345, which claims priority to U.S. Provisional Patent Application No. 61/506,316 filed Jul. 11, 2011, the entire contents of which are incorporated herein by reference.

BACKGROUND

This invention relates to sternal locators for IO devices that include a penetrator and more particularly relates to apparatuses, systems, and methods for sternal locators for placement of a conduit into an intraosseous space within a subject, such as within the sternum of a human patient. Embodiments of the present sternal locators are configured to control the depth at which the IO device is inserted and to stabilize the IO device after insertion.

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. According to the American Heart Association, more than 1,500,000 patients suffer from heart attacks (myocardial infarctions) every year, with over 500,000 of them dying from its devastating complications. Many wounded soldiers die within an hour of injury, usually from severe bleeding and/or shock. Many of these soldiers die unnecessarily because intravenous (IV) access cannot be achieved in a timely manner.

An essential element for treating many life threatening emergencies is rapid establishment of an IV line in order to administer drugs and fluids directly into a patient's vascular system. Whether in an ambulance by paramedics, in an emergency room by emergency specialists or on a battlefield by an Army medic, the goal is the same—quickly start an IV in order to administer lifesaving drugs and fluids. To a large degree, ability to successfully treat most critical emergencies is dependent on the skill and luck of an operator in accomplishing vascular access. While relatively easy to start an IV on some patients, doctors, nurses and paramedics often experience great difficulty establishing IV access in approximately 20% of patients. The success rate on the battlefield may be much lower. Sometimes Army medics are only about 29% successful in starting an IV line during battlefield conditions. These patients are often probed repeatedly with sharp needles in an attempt to solve this problem and may require an invasive procedure to finally establish intravenous access.

In the case of patients with chronic disease or the elderly, availability of easily accessible veins may be depleted. Other patients may have no available IV sites due to anatomical scarcity of peripheral veins, obesity, extreme dehydration or previous IV drug use. For such patients, finding a suitable site for administering lifesaving therapy often becomes a monumental and frustrating task. While morbidity and mortality statistics are not generally available, it is generally known that many patients with life threatening emergencies have died because access to the vascular system with lifesaving IV therapy was delayed or simply not possible.

The intraosseous (IO) space provides a direct conduit to a patient's vascular system and provides an attractive alternate route to administer IV drugs and fluids. Drugs administered intraosseously enter a patient's blood circulation system as rapidly as they do when given intravenously. In essence, bone marrow may function as a large non-collapsible vein. Intraosseous infusion has long been the standard of care in pediatric emergencies when rapid IV access is not possible. The U.S. military used hand driven IO needles for infusions extensively and successfully during World War II. However, such IO needles were cumbersome and difficult to use.

Proper placement of the intraosseous needle in the sternum is critical. If a user attempts to insert the needle in the wrong place, the bone might be too thick and therefore difficult for the needle to penetrate. Alternatively, the bone might be too thin; in such instances, the needle could completely penetrate the bone, missing the intraosseous region. Furthermore, placing the needle at an angle (not substantially perpendicular to the chest of the patient) may lead to the needle breaking or other complications.

SUMMARY

Disclosed are embodiments of sternal locators that can be used to insert a portion of an intraosseous (IO) device (e.g., a needle or needle set) into a patient at an appropriate depth (not over-inserted and not under-inserted) such that fluid can be delivered through the IO device and into an IO space within the patient (such as an IO space within the sternum of the patient), and that are configured to be inserted into the patient directly by the hand (e.g., gloved or ungloved) of a user and without the aid of a handle or other insertion device, that are configured to help stabilize the IO device once it has been inserted, and that are also configured to remain secured to the IO device and to the patient as fluid is delivered through the IO device.

Some embodiments of the present sternal locators are configured to be inserted into the chest of a human patient and include a stabilizer having at least one longitudinally-oriented tab configured to secure the stabilizer to an intraosseous (IO) device; and two or more (e.g., six) probes coupled to the stabilizer; where the stabilizer is configured to remain secured to the IO device after a portion of the IO device has been inserted into the patient and fluid is delivered through the IO device to an intraosseous space in the patient's sternum.

Some embodiments of the present sternal locators are configured to be inserted into the chest of a human patient and include a stabilizer having at least one longitudinally-oriented tab configured to secure the stabilizer to an intraosseous (IO) device; and two or more (e.g., six) probes coupled to the stabilizer; where the stabilizer is configured to be inserted into the patient through direct contact by a user.

Some embodiments of the present sternal locators are configured to be inserted into the chest of a human patient and include a stabilizer that has a circumferential collar that includes a collar contact surface configured to contact a portion of an intraosseous (IO) device, a passageway configured to receive a penetrator of the IO device, and one or more tabs configured to secure the stabilizer to the IO device; a flange projecting from the circumferential collar, where the flange includes an alignment feature spaced apart from the passageway and configured to align with the sternal notch of the patient, and an underside opposite the collar contact surface; and two or more (e.g., six) probes coupled to the stabilizer.

Some embodiments of the present systems may include any of the present sternal locators and a penetrable material (e.g., foam) that is configured such that the probes of the sternal locator may be inserted in the penetrable material and not be otherwise exposed, and an open container having a reservoir into which the penetrable material may be placed and held through, for example, an adhesive member attached to both the bottom of the penetrable material and to the bottom surface of the reservoir or, in other embodiments, friction between the penetrable material and the container surface forming the reservoir. Some such embodiments may further include a package (e.g., a flexible package, such as one that does not include a tray, such as a plastic tray) containing at least the sternal locator, the penetrable material, and the open container, and may in more specific embodiments also include one of the disclosed IO devices and/or instructions for use, which may be on the outside of the package, on the sternal locator, and/or on an insert contained within the package.

Some embodiments of the present systems are for accessing the bone marrow of a human's sternum and include an intraosseous (IO) device that has a penetrator having a tip, and a hub coupled to the penetrator, the hub comprising a flanged portion; and a sternal locator configured to be inserted into the chest of a human patient and coupled to the IO device, where the sternal locator includes a stabilizer having at least one longitudinally-oriented tab configured to secure the stabilizer to the IO device, and two or more (e.g., six) probes coupled to the stabilizer, each probe having a probe tip; where the tip of the penetrator will protrude 6 to 8 millimeters beyond at least one of the probe tips when the IO device is secured to the sternal locator. Some embodiments of the present systems may also include a penetrable material (e.g., foam) that is configured such that the probes of the sternal locator may be inserted in the penetrable material and not be otherwise exposed, and an open container having a reservoir into which the penetrable material may be placed and held through adhesive and/or friction between the penetrable material and the container surface forming the reservoir. In some embodiments, the sternal locator includes multiple longitudinally-oriented tabs spaced apart from each other and configured to secure the stabilizer to the IO device.

Some embodiments of the present methods are for accessing the bone marrow in the sternum of a human patient, and include locating the sternal notch on the chest of the patient; placing a sternal locator having an alignment feature on the chest of the patient such that the alignment feature is aligned with the sternal notch, the sternal locator including a stabilizer having one or more longitudinally-oriented tabs spaced apart from each other and configured to secure the stabilizer to an intraosseous (IO) device, and two or more (e.g., six) probes coupled to the stabilizer; contacting the sternal locator directly with a gloved or ungloved hand of a user and pushing the sternal locator against the chest of the patient until the two or more (e.g., six) probes penetrate the skin of the patient and contact the anterior compact bone of the patient's sternum; inserting an intraosseous (IO) device into the patient, the IO device comprising a penetrator having a tip, and a hub coupled to the penetrator, the hub comprising a flanged portion, where the inserting includes inserting the penetrator through a passageway in the sternal locator; and applying pressure to the IO device until all of the one or more longitudinally-oriented tabs engage the flanged portion of the hub.

Some embodiments of the present methods may be for training purposes and may include coupling an intraosseous (IO) device to a sternal locator, the sternal locator including a stabilizer having one or more longitudinally-oriented tabs configured to secure the stabilizer to an intraosseous (IO) device, and two or more (e.g., six) probes coupled to the stabilizer, the IO device comprising a penetrator having a tip, and a hub coupled to the penetrator, the hub comprising a flanged portion; contacting at least one of the one or more longitudinally-oriented tabs with a removal tool and pushing or threading the removal tool distally, thereby spreading the at least one of the one or more tabs outwardly and distally relative to the hub until the tab or tabs are sufficiently distal of the hub that the IO device can be removed; removing the removal tool, and removing the hub and penetrator. In some embodiments, the sternal locator and IO device can be inserted in penetrable material during the contacting step.

The IO devices in this disclosure include those with elements containing a passageway that can be placed in fluid communication with a fluid source and with an IO space within a patient (such as elements that are hollow and have open ends and that are inserted into the IO space together with an inner penetrator (like a stylet) and elements that have a closed tip but a passageway open in close proximity to the closed tip), where the portion of the element that remains in the patient after insertion of the IO device is rigid, unlike a plastic flexible tube.

The term "coupled" is defined as connected, although not necessarily directly, and not necessarily mechanically.

The terms "a" and "an" are defined as one or more unless this disclosure explicitly requires otherwise.

The term "substantially" and its variations (e.g. "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present sternal locators and the disclosed intraosseous devices, and their components, shown in the figures are drawn to scale.

FIG. 9 is a top view of the stabilizer of FIG. 8A.

FIG. 10 is a bottom view of the stabilizer of FIG. 8A.

FIG. 11 is a cross-sectional view of the stabilizer of FIG. 8A taken along line X-X' in FIG. 9.

FIG. 16A is a top perspective view of one of the present open containers holding one of the present penetrable materials.

FIG. 16B is a top perspective view of the open container shown in FIG. 16A.

FIG. 16C is a top perspective view of the penetrable material shown in FIG. 16A.

DETAILED DESCRIPTION

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

As used in this disclosure, the terms "proximal" and "distal" are used in relation to the orientation of a given feature relative to a user of the disclosed devices, rather than to the subject (e.g., the patient) on which those devices are used.

Figure 1:
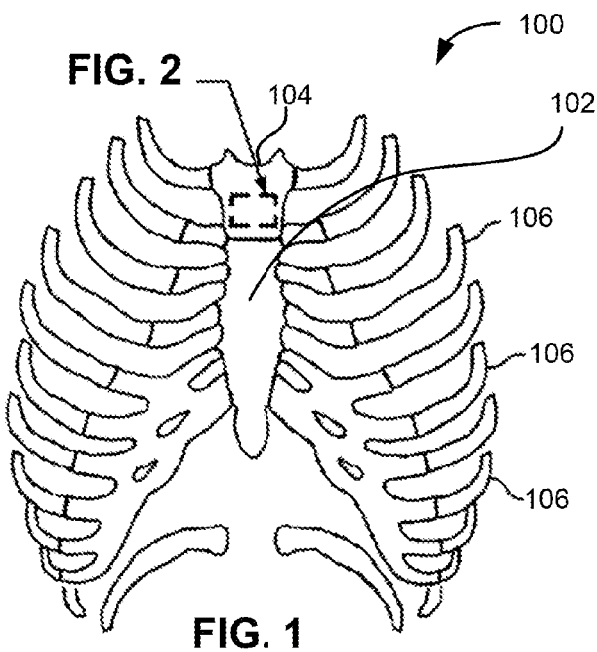
FIG. 1 is a schematic view of the ribcage of a human.

FIG. 1 depicts a schematic view of the ribcage of a human 100. The sternum 102 is a flat, narrow bone between the ribs 106 comprising three segments: the manubrium, the body, and the xiphoid process. The sternum also comprises a sternal notch 104 (also called the "suprasternal notch" or the "jugular notch"), which is a U-shaped anatomical feature located above the sternum, below the throat, and between the clavicles.

Figure 2:
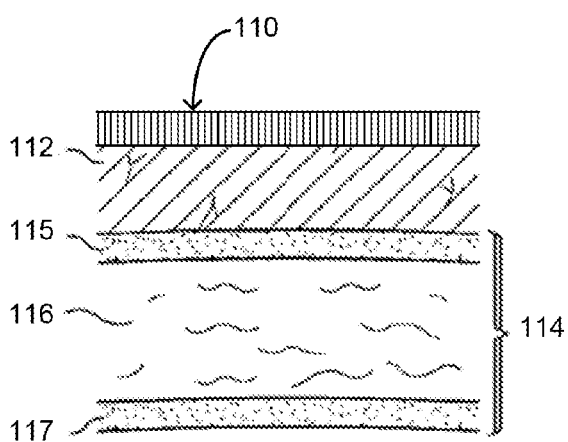
FIG. 2 is a cross-section view of a region of the sternum of a human.
Figure 3B:
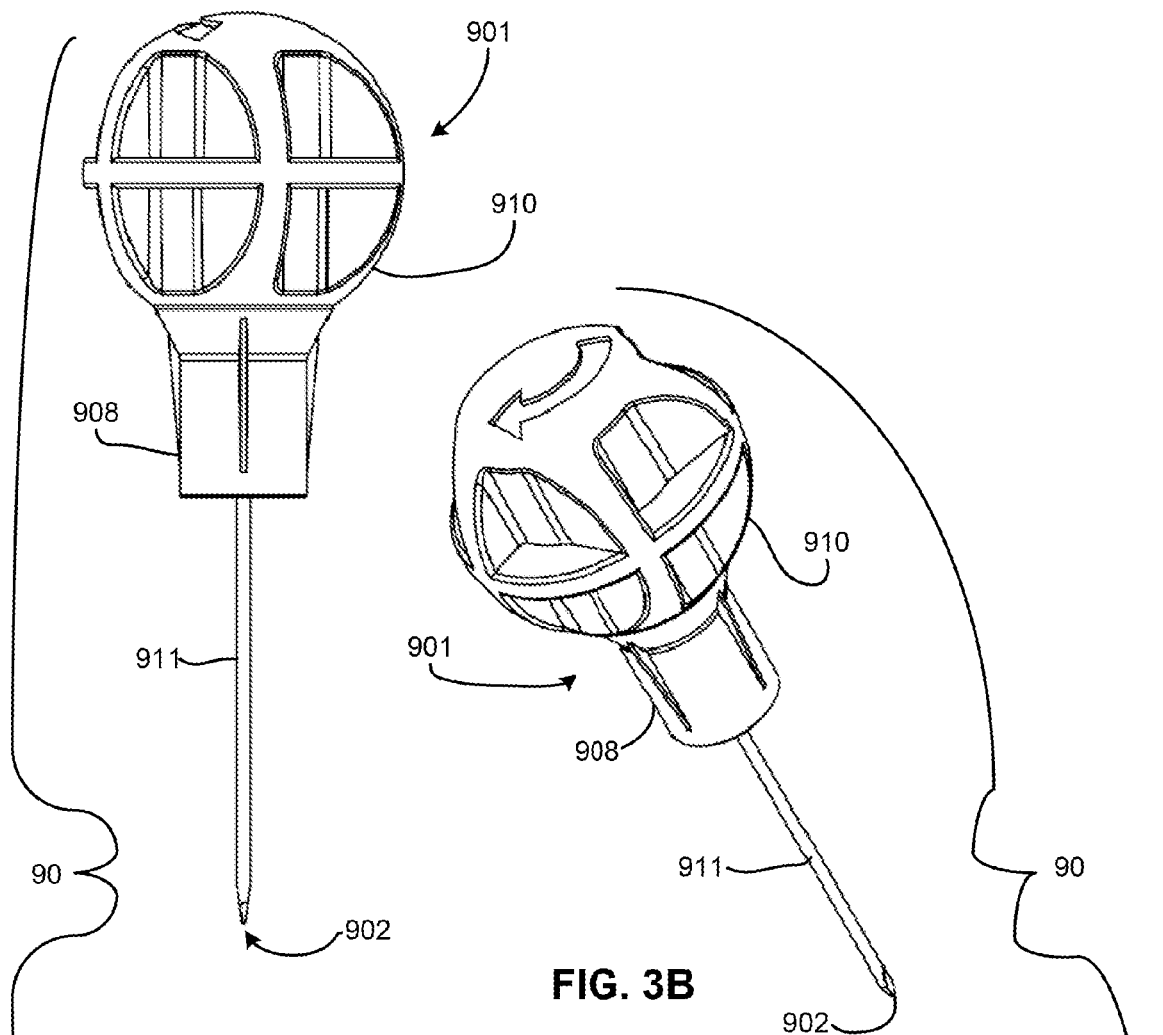
FIG. 3B is a perspective exploded view of the IO device of FIG. 3A.
Figure 3A:
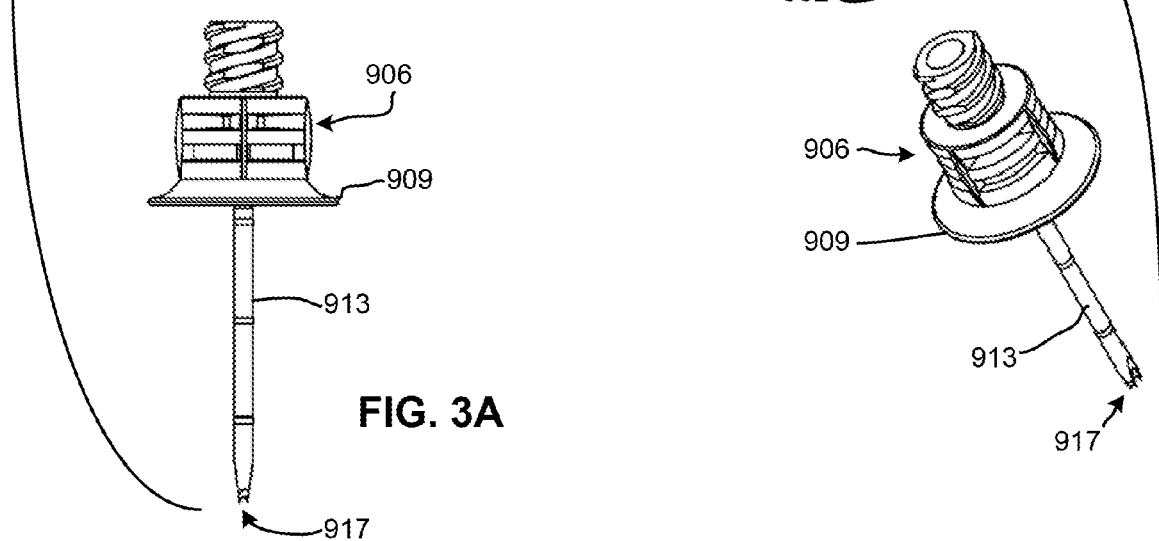
FIG. 3A is a front view exploded view of one embodiment of an intraosseous (IO) device that can be used with embodiments of the present sternal locators, the IO device including a manual driver portion with an inner penetrator and an outer penetrator hub portion with an outer penetrator.
Figure 3C:
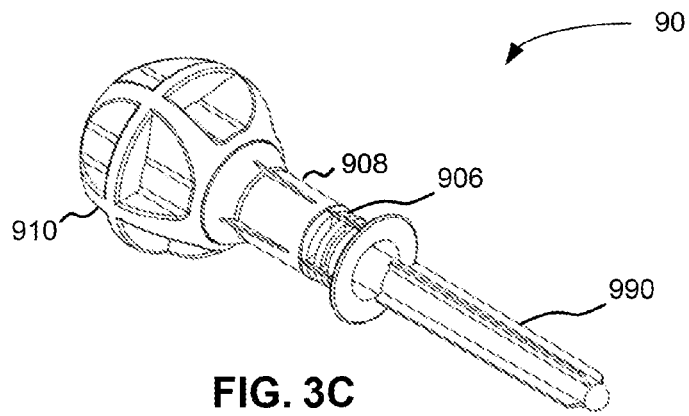
FIGS. 3C-3E depict various views of the IO device of FIG. 3A including a removable cover.
Figure 3D:
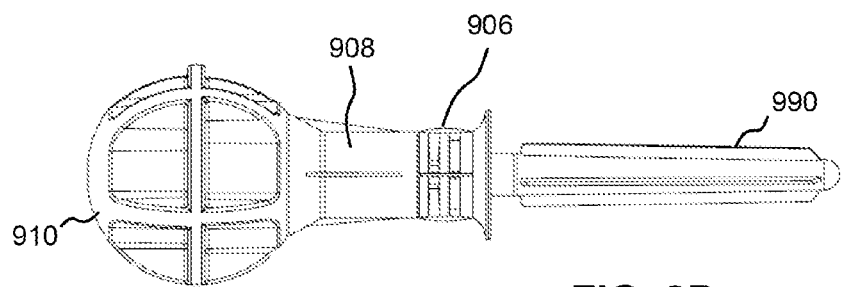
Figure 3E:
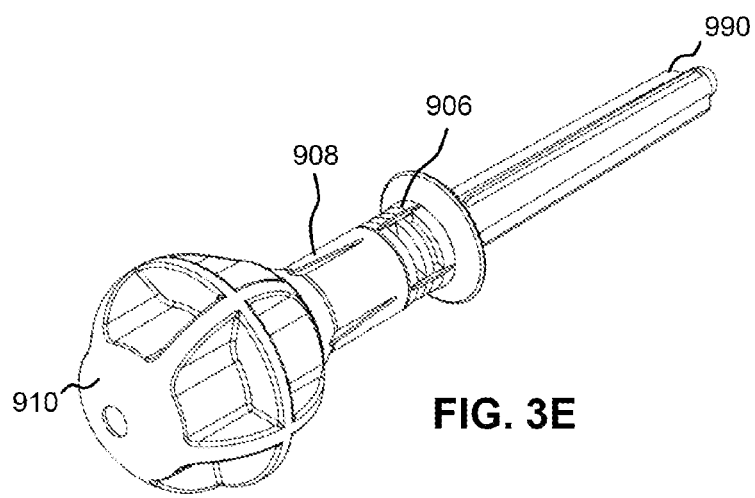
Figure 3F:
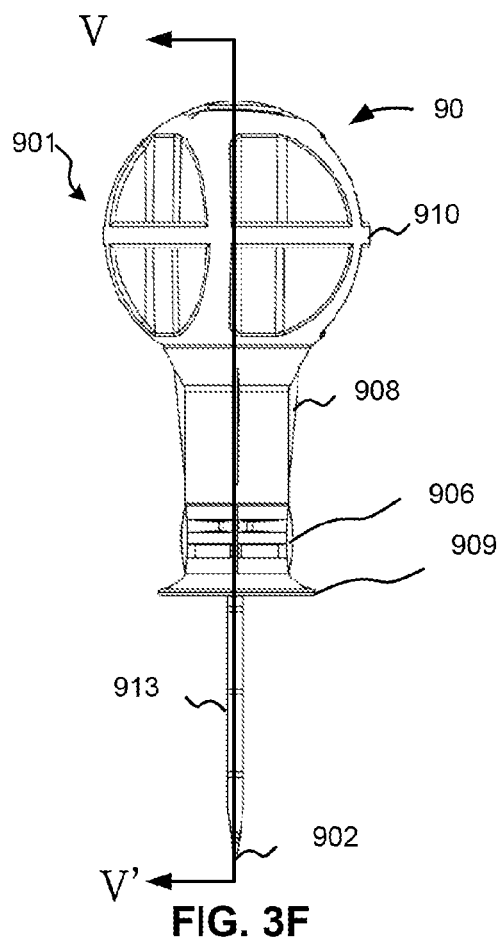
FIG. 3F is a front assembled view of the IO device of FIG. 3A without the removable cover.
Figure 3G:
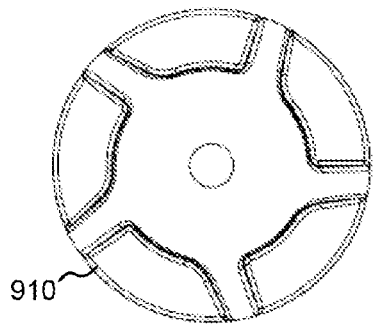
FIG. 3G depicts a top view of the IO device of FIG. 3A.
Figure 3H:
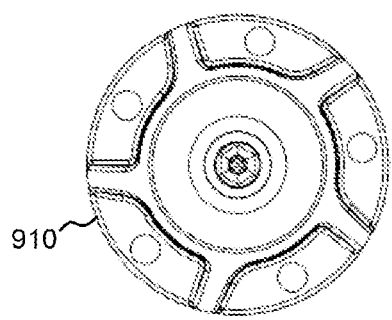
FIG. 3H depicts a bottom view of the IO device of FIG. 3A.
Figure 3I:
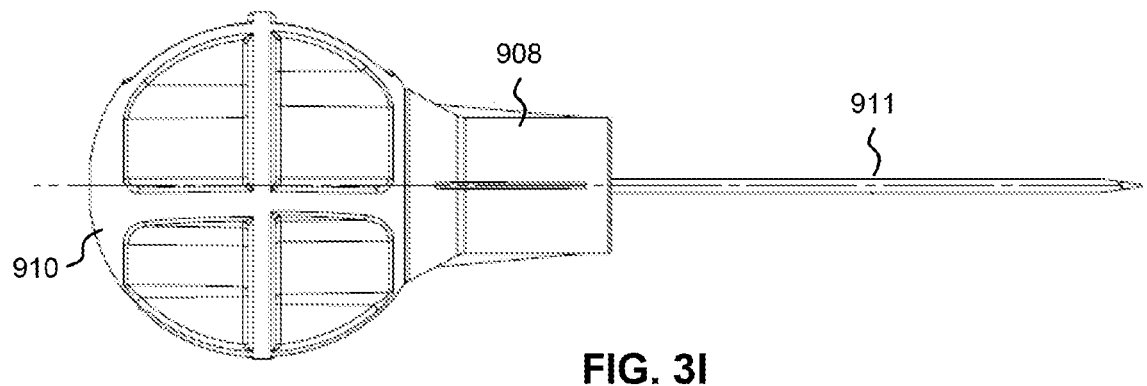
FIG. 3I depicts the manual driver portion of the IO device of FIG. 3A.
Figure 3J:
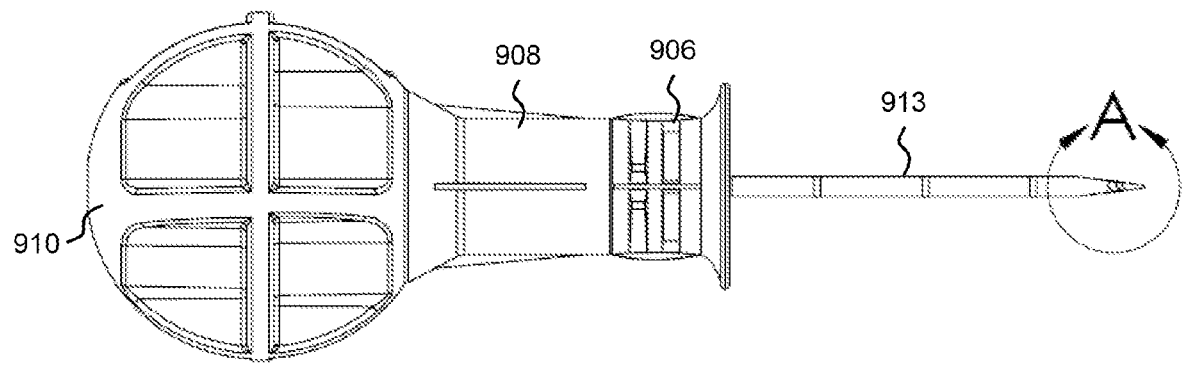
FIG. 3J depicts a side view of the IO device of FIG. 3A.
Figure 3K:
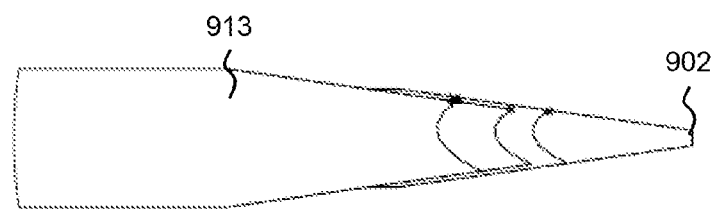
FIG. 3K depicts a detailed view of the inner penetrator and outer penetrator of the IO device of FIG. 3J.
Figure 3L:
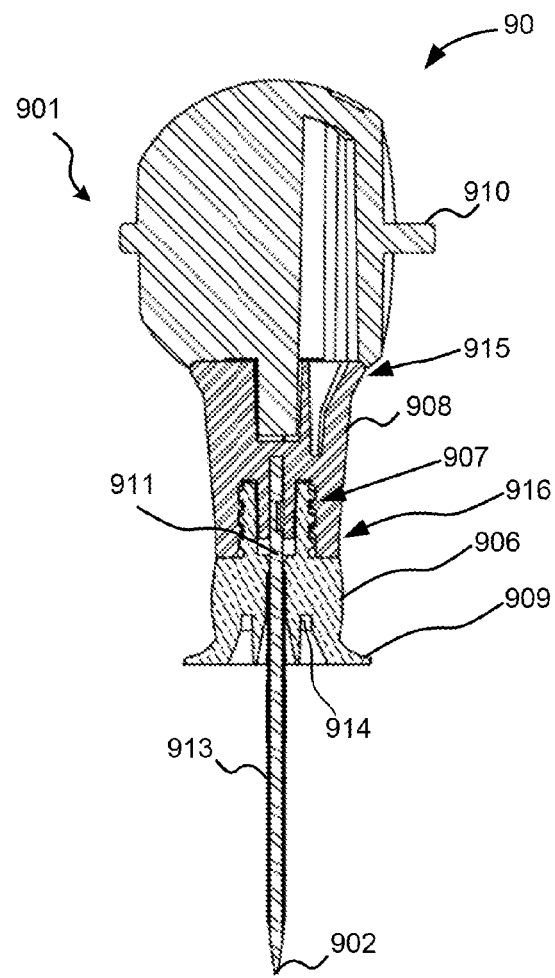
FIG. 3L is a cross-sectional view of the IO device of FIG. 3A taken along line V-V' in FIG. 3F.
Figure 4A:
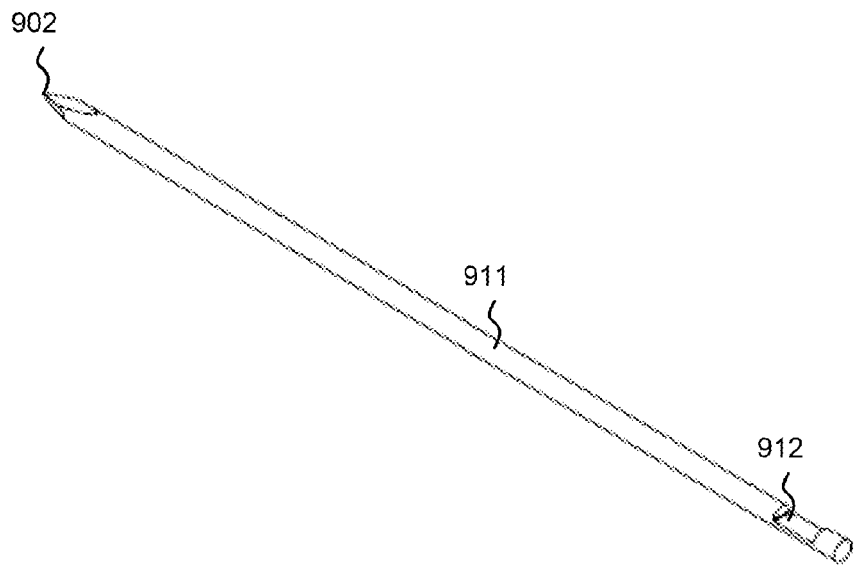
FIGS. 4A-4C depict various views of the inner penetrator of the manual driver of the IO device of FIG. 3A.
Figure 4B:
Figure 4C:

FIG. 2 shows a cross-sectional view of a portion of the sternum 100. Skin 110 overlays a layer of subcutaneous tissue 112, which in turn overlays bone 114. Bone 114 includes an intraosseous space 116 bounded by anterior compact bone (anterior cortex, in the depicted embodiment) 115 and posterior compact bone (posterior cortex, in the depicted embodiment) 117. Intraosseous space 116 is the region between the anterior and posterior cortex. Bone marrow includes blood, blood forming cells, and connective tissue found in the intraosseous space.

Anterior compact bone 115 and posterior compact bone 117 are each approximately 2.0 millimeters (mm) thick and intraosseous space 116 is approximately 10.0 mm thick in about 95% of adult patients. Thus, the total thickness of bone 114 is approximately 14.0 mm. The target zone within the intraosseous space 116 is the center, which is approximately 7.0 mm from the upper surface of anterior compact bone 115 in 95% of adult patients.

Intraosseous space 116 may be accessed by an IO device. The term "intraosseous (IO) device" in this application includes any hollow needle, hollow drill bit, penetrator assembly, bone penetrator, catheter, cannula, trocar, inner penetrator, outer penetrator, needle or needle set operable to provide access to an intraosseous space or interior portions of a bone. A wide variety of trocars, spindles and/or shafts may be disposed within a cannula during insertion at a selected insertion site. Such trocars, spindles and shafts may also be characterized as inner penetrators. Inner penetrators can comprise various lengths including, but not limited to, 20 to 50 millimeters (e.g., between 35 and 40 mm, 38.5 mm, and/or the like). A catheter, cannula, hollow needle or hollow drill bit may sometimes be characterized as an outer penetrator. FIGS. 3A-5E illustrate an embodiment of an IO device and its components, the IO device configured for manual insertion into a subject's intraosseous space, the IO device comprising a penetrator. Intraosseous device 90 comprises a manual driver 901 that includes a handle or grip 910 (which can also be termed a driver), which is coupled (more specifically, attached) to inner penetrator hub 908, which is attached to inner penetrator 911, which, for example, may take the form of any suitable stylet or trocar. Inner penetrator 911 can have, for example, notch 912 configured to assist in coupling inner penetrator hub 908 to inner penetrator 911 (e.g., such that inner penetrator hub 908 can be overmolded over inner penetrator 911 the material from which the inner penetrator hub may be molded to extend into notch 912). IO device 90 also includes an outer penetrator hub 906 that is coupled (more specifically, attached) to outer penetrator 913, which, may, for example, take the form of a hollow tube, such as cannula (e.g., a metal cannula), or a hollow drill bit, and which may be configured (e.g., to possess sufficient rigidity) such that outer penetrator 913 will not buckle or otherwise be damaged as it is inserted through anterior compact bone together with inner penetrator 911. Outer penetrator hub 906 includes proximal end 907 and distal end 909 that is configured with a flange in the depicted embodiment. Proximal end 907 of outer penetrator hub 906 and distal end 916 of inner penetrator hub 908 may be configured as complimentary connectors (with, for example, distal end 916 being configured as a male Luer connector and proximal end 907 being configured as a female Luer connector, though these configurations could be reversed in other embodiments) to allow manual driver 901 to be removably coupled to outer penetrator 913. For example, outer penetrator hub 906 (and, more specifically, proximal end 907 of outer penetrator hub 906) may include an external surface 907t that is threaded and that is proximate an inwardly-tapered passageway 907p that is in fluid communication with the passageway of outer penetrator 913 (see FIG. 5B); and inner penetrator hub 908 (and, more specifically, distal end 916 of inner penetrator hub 908) may include an internal surface that is threaded to mate with the threaded, external surface of hub 906 and that is proximate a male projection that is tapered to match the taper of the inwardly-tapered passageway of hub 906 (these surfaces are shown but not labeled in FIG. 3L).

Figure 20A:
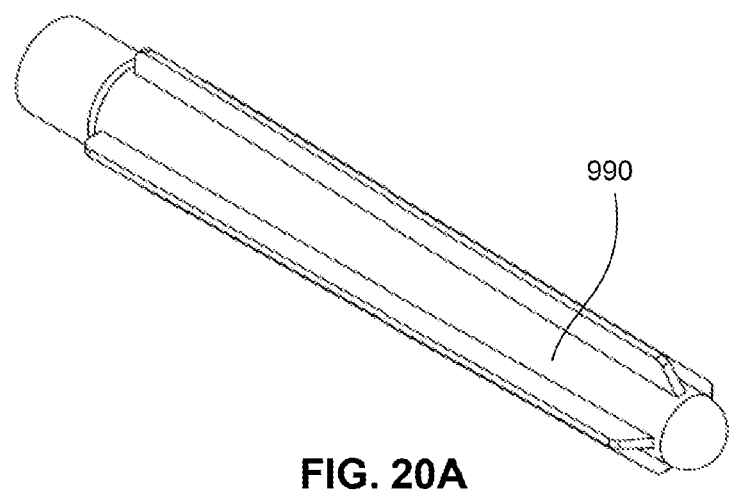
FIGS. 20A-20C depict various views of an embodiment of a removable cover configured to be coupled to an outer penetrator hub of the present IO devices to cover at least one of an inner penetrator and an outer penetrator of the IO device.
Figure 20B:
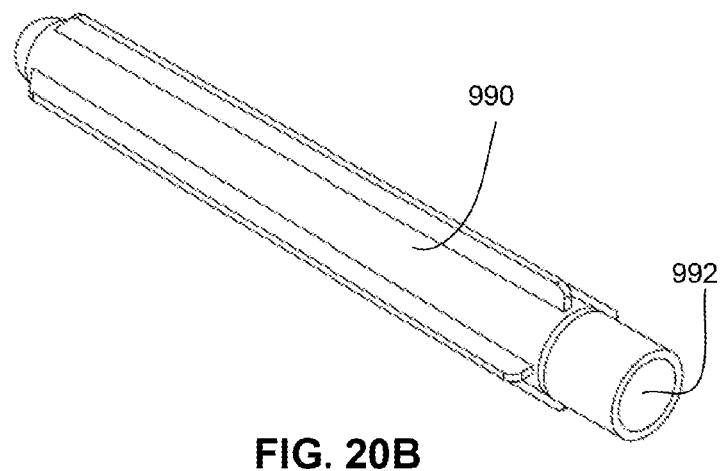
Figure 20C:
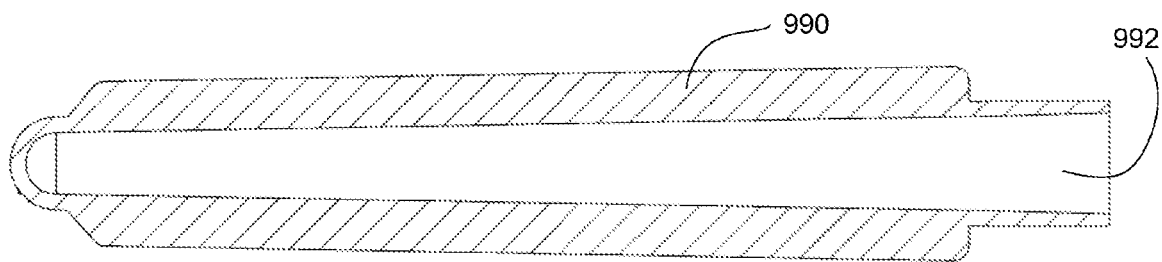

In certain embodiments, IO device 90 comprises a removable cover 990 (also depicted in FIGS. 20A-20C), the proximal end of which can be coupled through a friction fit to hub 906 via groove 914 in hub 906. When driver 901 and outer penetrator 913 are coupled to each other, as shown in FIGS. 3A-5, inner penetrator 911 of driver 901 is disposed within the passageway of outer penetrator 913, and tip 902 of inner penetrator 911 extends beyond the distal end 917 of outer penetrator 913. For example, inner penetrator 911 and/or outer penetrator 913 can be disposed within removable cover 990 (e.g., through opening 992, as shown in FIGS. 20B-20C). When removable cover 990 is coupled to outer penetrator hub 906, the removable cover will protect a user or operator of IO device 90 (as well as a subject on which the device will be used) from being inadvertently stuck by tip 902 of inner penetrator 911.

In the illustrated embodiment, grip 910 and hub 908 are attached to each other through a bond created through an ultraviolet (UV)-curable adhesive. In other embodiments, grip 910 and hub 908 may be integral with each other (such as through injection molding), force coupled, or otherwise adhered to one another, while in other embodiments, grip 910 and hub 908 may be removably coupled to each other such that they can be separated without destroying, damaging or otherwise impairing the function of either for re-use. In still other embodiments, grip 910 may be coupled directly to outer penetrator hub 906 such that there is no intervening inner penetrator hub 908 (with inner penetrator 911 being attached directly to grip 910 in such embodiments).

Figure 5A:
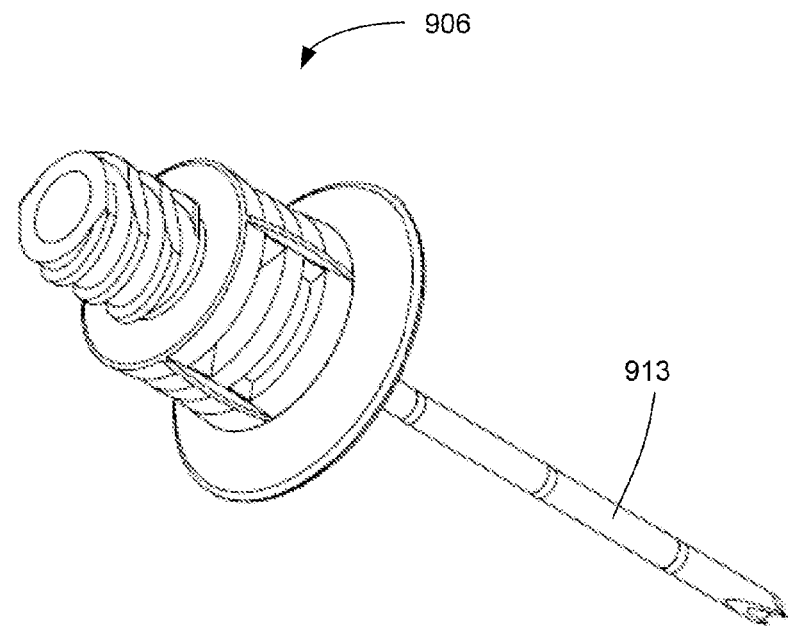
FIGS. 5A-5E depict various views of the outer penetrator hub of the IO device of FIG. 3A.
Figure 5B:
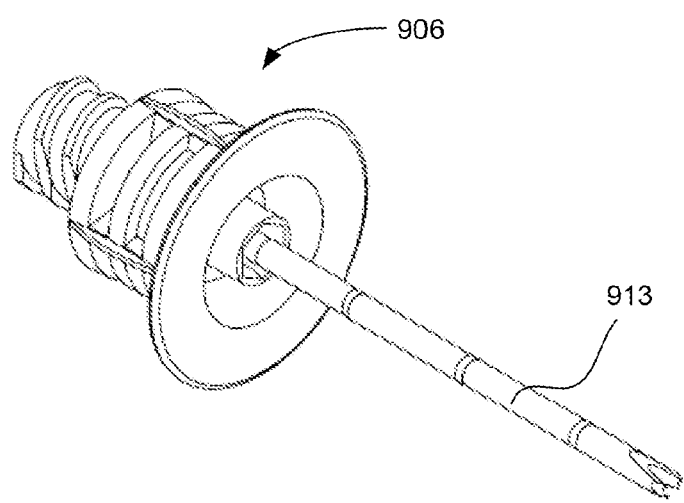

Tip 902 of inner penetrator 911 is pointed and configured to allow IO device 90 to be driven into an intraosseous space, such as intraosseous space 116. Inner penetrator 911 fits closely within outer penetrator 913 such that inner penetrator 911 prevents outer penetrator 913 from becoming clogged with tissue (e.g., skin, bone) as IO device 90 is driven into a subject (e.g., a patient). Tip 902 and distal end 917 of outer penetrator 913 can, in some embodiments where both inner penetrator 911 and outer penetrator 913 are made of a suitable metal, be ground together. Once IO device 90 is properly positioned, manual driver 901 can be disengaged from outer penetrator hub 906 such that proximal end 907 (which may take the form of a male Luer lock) is exposed and a conduit is formed from outer penetrator hub 906 through outer penetrator 913 to intraosseous space 116, as shown in FIG. 5B (adhesive member 50 and top layer 40 have been omitted from FIG. 5B for clarity). A fluid source (not shown) may then be coupled to proximal end 907 to deliver fluid through outer penetrator 913 into intraosseous space 116.

Figure 5C:
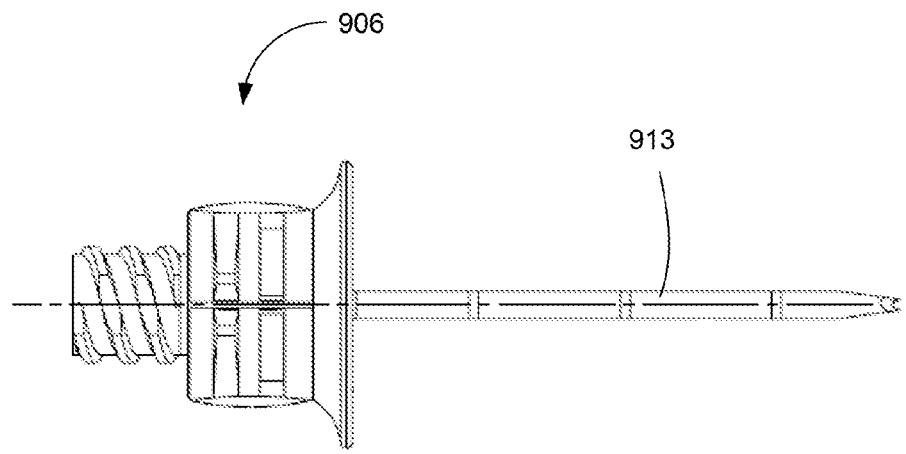
Figure 5D:
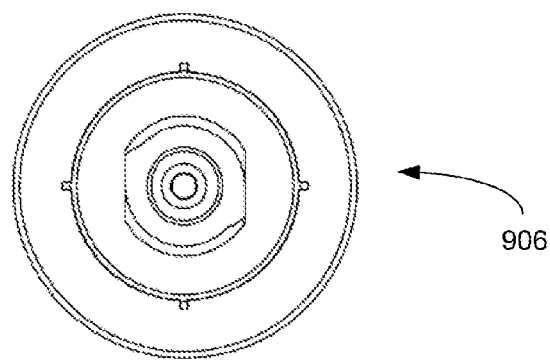
Figure 5E:
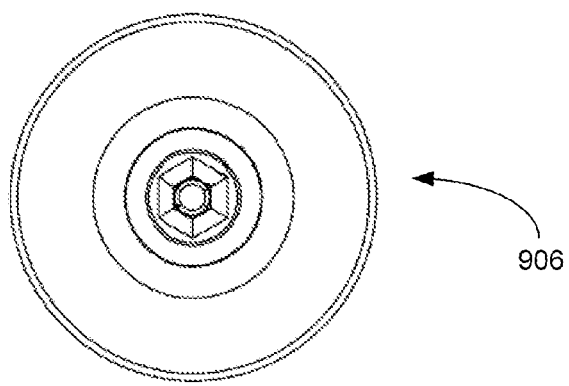

Any suitable configuration for IO device 90 may be used (adjusted to address the depth penetration issues discussed in this disclosure), including, for example, the IO devices shown in FIGS. 5C and 6D of U.S. Patent Application Publication No. US 2007/0270775 A1, which is incorporated by reference.

FIGS. 6-12N depict various views of embodiments of the present sternal locators (e.g., sternal locator 10, sternal locator 10a, etc.) or components of the present sternal locators. For example, FIGS. 6-11 depict various views a first embodiment 10 of the present sternal locators and components thereof. In the illustrated embodiment, sternal locator 10 comprises stabilizer 20, a flange portion of which is located between and coupled to a top sheet 40 and an adhesive member 50. Top sheet 40 and adhesive member 50 are coupled to each other in this embodiment. Adhesive member 50 comprises an adhesive configured to adhere sternal locator 10 to a subject during use (e.g., to the skin on the chest of a human patient).

Stabilizer 20 comprises a circumferential collar 210 and a flange 230 projecting from the circumferential collar 210. Flange 230 comprises a top surface 232 and an underside 236. Flange 230 also comprises an alignment feature 234. In the embodiment shown, circumferential collar 210 comprises a collar contact surface 212 and a cylindrical protrusion 213 having a passageway 214 extending through the stabilizer, as well as three (longitudinally-oriented) tabs 216 that are spaced apart from each other, such as circumferentially-spaced apart from each other at 120 degree intervals (as shown in FIG. 9). In other embodiments, there may be more or fewer tabs 216 (e.g., 1, 2, 4, 5, 6, 7, 8, or more tabs). Passageway 214 extends from collar contact surface 212 to underside 236. Collar contact surface 212 is an example of a surface configured to contact a portion of an IO device to impede further insertion of the IO device. Collar contact surface 212 is also an example of a proximal-facing surface adjacent a passageway configured to receive a penetrator of an IO device.

Figure 6:
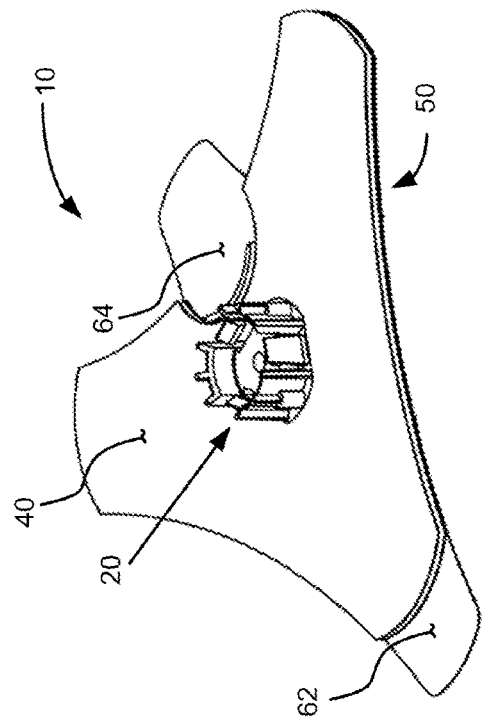
FIG. 6 is a perspective view of one embodiment of the present sternal locators.
Figure 8A:
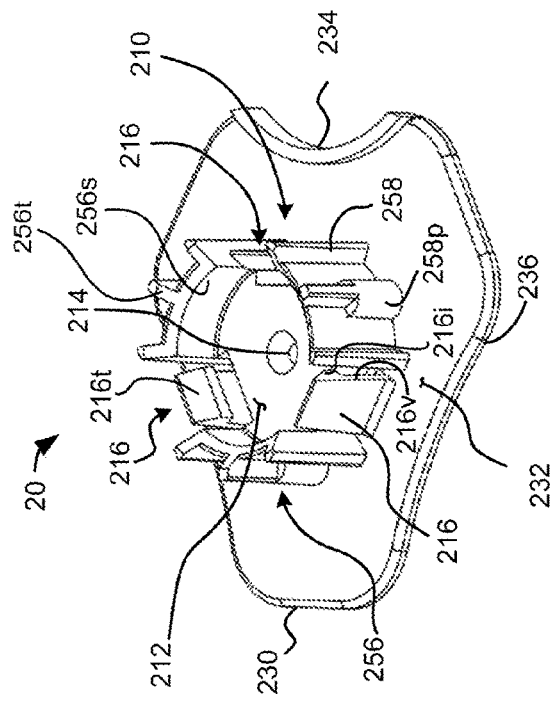
FIG. 8A is a top perspective view of one embodiment of the present stabilizers for use in at least some embodiments of the present sternal locators, such as, for example, as shown in the sternal locator of FIG. 6.
Figure 7:
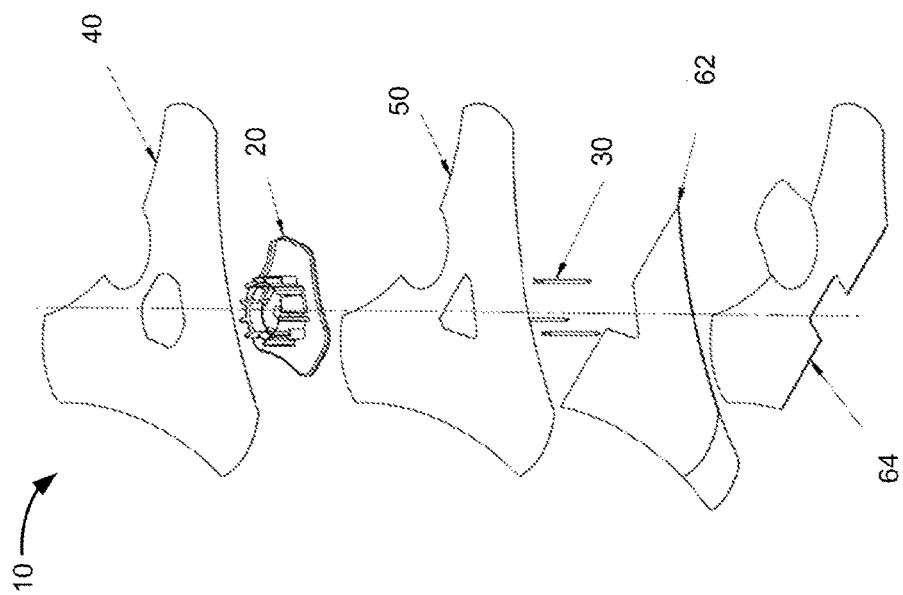
FIG. 7 is an exploded view of the sternal locator of FIG. 6.
Figure 8B:
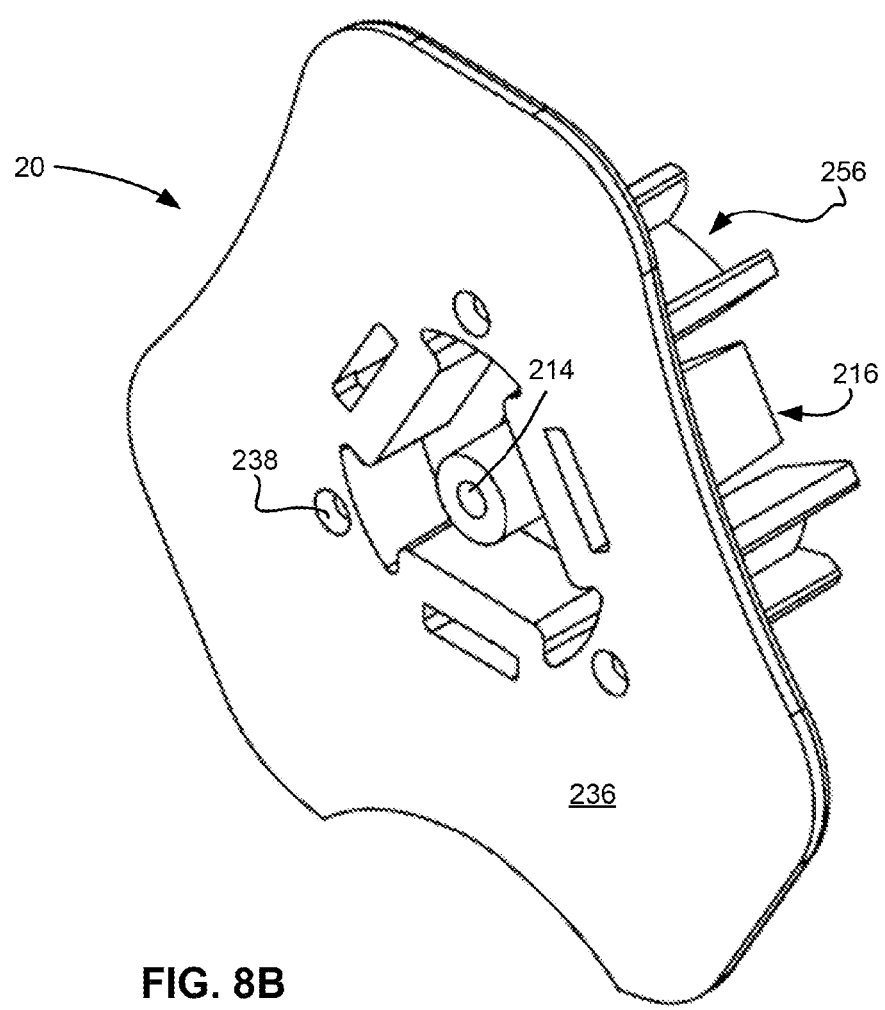
FIG. 8B is a bottom perspective view of the stabilizer of FIG. 8A.

In some embodiments, top sheet 40 comprises single-sided tape, such as 3M 1526 polyethylene single coated tape. In such embodiments, top sheet 40 is oriented such that the adhesive side of the tape couples top sheet 40 to top surface 232 of flange 230 and to adhesive member 50. Adhesive member 50 may comprise any standard medical grade adhesive. In specific embodiments, the adhesive member comprises double-sided tape, such as 3M 1522 transparent polyethylene double coated tape. In such embodiments, one side of adhesive patch 50 is coupled both to underside 236 of flange 230 and to top sheet 40, while the other side of adhesive member 50 is coupled to at least one liner (e.g., a release liner). As shown in FIGS. 6 and 7, adhesive member 50 is coupled to a removable first liner 62 and a removable second liner 64. Removable liners 62, 64 cover the bottom adhesive side of adhesive member 50 (e.g., to prevent sternal locator 10 from undesired sticking). When sternal locator 10 is ready to be used, liners 62, 64 can be removed by a user and sternal locator 10 can be placed on, for example, the chest of a patient.

Other embodiments of the present sternal locators may not include top sheet 40 or adhesive member 50. For example, in some embodiments, sternal locator 10 may lack any adhesive features for coupling the template to the chest of a patient. In still other embodiments, underside 236 of flange 230 may be coated with an adhesive directly applied to stabilizer 20 (that is, without requiring a tape layer as discussed above). In such embodiments, one or more liners may be coupled directly to stabilizer 20 to prevent undesired sticking. Embodiments of the present sternal locators that include an adhesive—such as one applied directly to the underside of the flange of the stabilizer or one on the bottom (distal) surface of an adhesive member—may be characterized as being configured to adhere to skin on a subject.

FIGS. 8-11 illustrate one of the present embodiments of stabilizer 20. Sternal locator 10 is configured to be placed on the chest of a subject (e.g., a human patient) at a location near sternum 114 and aligned with sternal notch 104. Sternal locator 10 is also configured to ensure proper placement of an IO device in intraosseous space 116.

Collar 210 is, and more specifically the one or more tabs 216 of collar 210 are configured to couple (e.g., secure) stabilizer 20 to an IO device. For example, each tab 216 has an inwardly-projecting portion 216i that, in the depicted embodiment, includes a surface 216s that is configured to overlie a portion of hub 906 (and, more specifically, the flange portion of distal end 909 of outer penetrator hub 906) of IO device 90. At least a portion of each surface 216s may be oriented at a non-zero (e.g., perpendicular) angle to the direction of insertion of IO device 90. More particularly, each surface 216s may be configured with a shape that complements the shape of the portion of distal end 909 of outer penetrator hub 906 it will contact after IO device 90 is inserted, which portion may be on a proximally-facing surface of outer penetrator hub 906. As a result, surfaces 216s are configured to resist or impede travel of outer penetrator 913 after outer penetrator 913 is inserted into intraosseous space. In the embodiment shown, each tab 216 (and, more specifically, each vertical component 216v of each tab 216) is configured to flex outward away from the center of stabilizer 20 as inwardly-tapered exterior surface 216t of portion 216i contacts a distally-facing surface of the flanged portion of distal end 909 of outer penetrator hub 906, then snap inward as surface 216s passes over that flanged portion, locking IO device 90 in place. One skilled in the art will understand that the number of tabs used may be adjusted to best suit the shape of the IO device being used.

The rigidity of tabs 216 serves to stabilize the IO device to which the sternal locator is coupled, both by resisting any outward longitudinal movement of the IO device (meaning movement out of the intraosseous space along the direction of insertion) as well as any movement that would otherwise result from the IO device canting from side-to-side or otherwise moving laterally. Collar 210 also includes longitudinally-oriented elements 256 that have inwardly-tapered surfaces 256t and curved inner surfaces (which are shaped like the inside of a cylinder) 256s. These elements are taller than tabs 216 and function to guide the IO device to the proper location as it enters the space bounded by collar 210, which also helps to prevent damage to tabs 216, and they help to resist any lateral pitching or movement of the IO device. Each element 256 includes multiple longitudinally-oriented ribs 258 that serve to increase the rigidity (and tendency to resist lateral bending) of element 256, the middle rib of which includes a lower portion 258p that is enlarged because it surrounds a portion of probe 30 (discussed below).

In the illustrated embodiment, alignment feature (or notch) 234 of stabilizer 20 is an arc-shaped portion of flange 230. Alignment feature 234 is configured to approximate the shape of sternal notch 104 of a human patient and is configured to indicate proper placement of sternal locator 10. The sternal locator depicted in the figures is properly placed on the chest of a patient when the sternal notch is visible and at least partially (and, preferably, completely) bounded by alignment feature 234 and the stabilizer is placed over the sternum.

The most inwardly-curved portion of alignment feature 234 is spaced a distance $D_A$ from the center of hole 214 (that is, $D_A$ is the shortest distance between hole 214 and alignment feature 234). In certain embodiments, $D_A$ is about 21 mm. In other embodiments, $D_A$ may range from about 10 mm to about 35 mm. The outer edge of flange 230 may be 7 mm from the nearest location on the closest tab 216, such that distance $D_F$ may be 7 mm. In other embodiments, $D_F$ may range from 0 to 15 mm. Some other embodiments of the present stabilizers 20 may not include flange 230.

In the illustrated embodiment, stabilizer 20 comprises multiple (specifically, three in the depicted embodiment) openings 238 in underside 236. A recess 239 extends from each opening 238 that is configured to receive a probe 30. Other embodiments may comprise more or fewer recesses (and associated openings) configured to receive more or fewer probes 30.

Figure 12A:
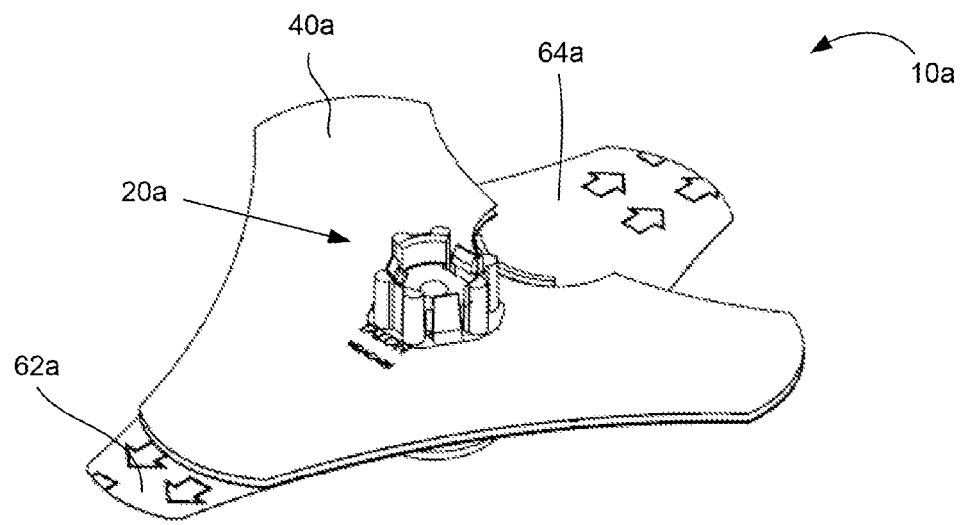
FIGS. 12A-12C depict various views of another embodiment of the present sternal locators.
Figure 12B:
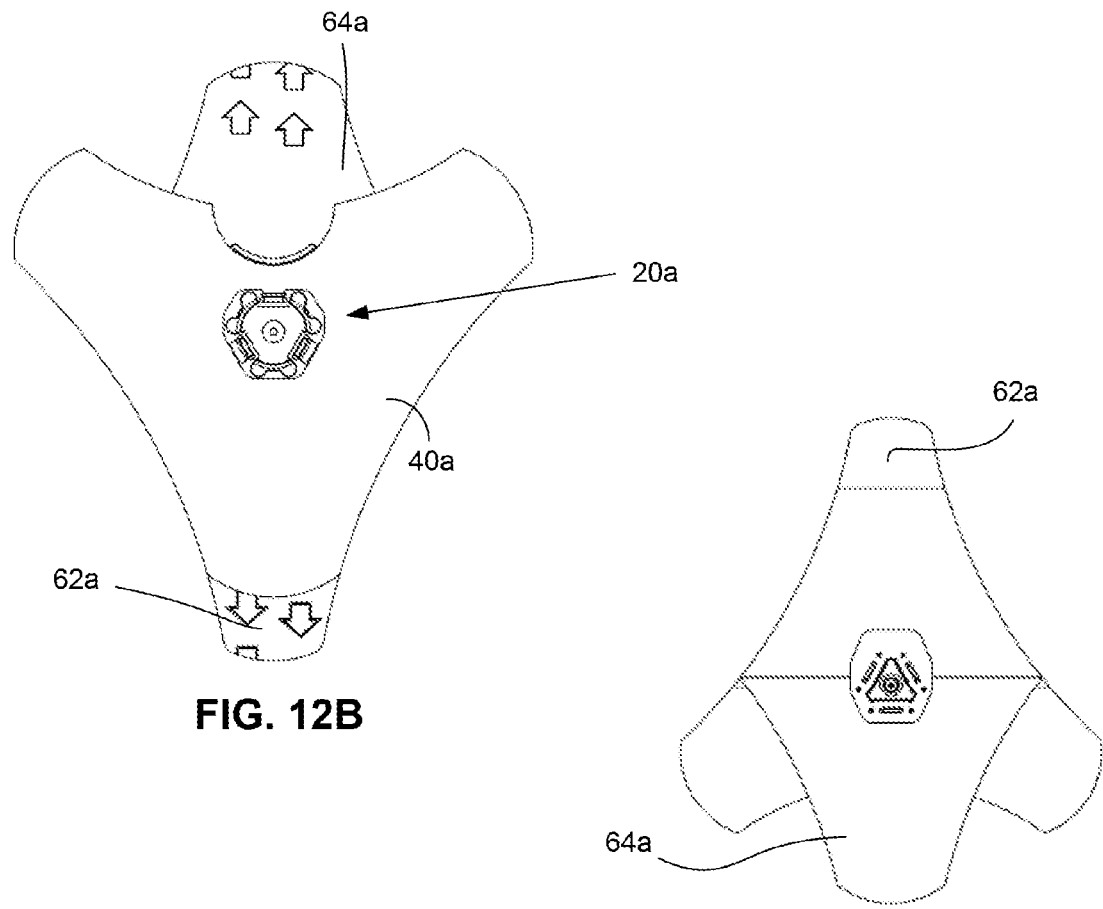
Figure 12C:
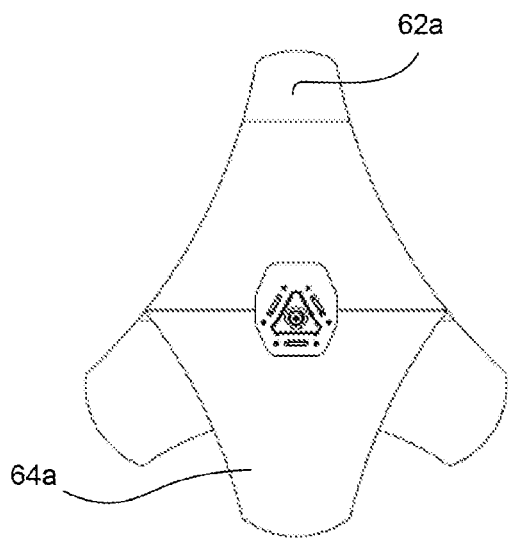
Figure 12D:
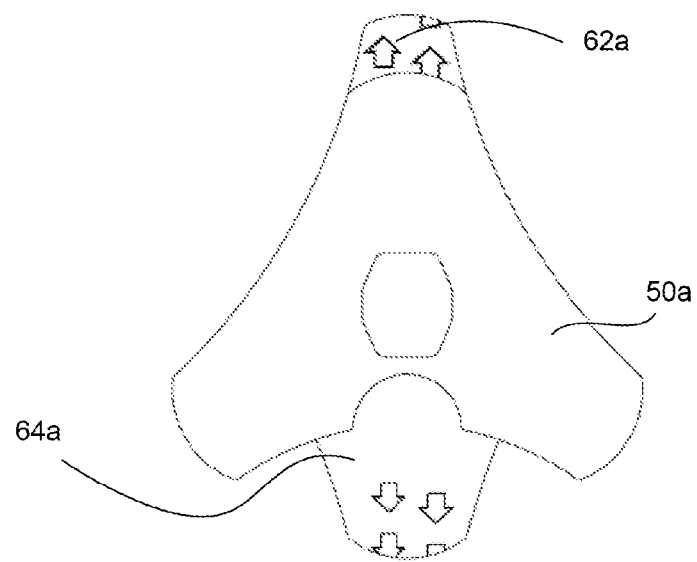
FIGS. 12D-12H depict various views of top sheets, adhesive members, and/or removable liners of the sternal locator of FIGS. 12A-12C.
Figure 12E:
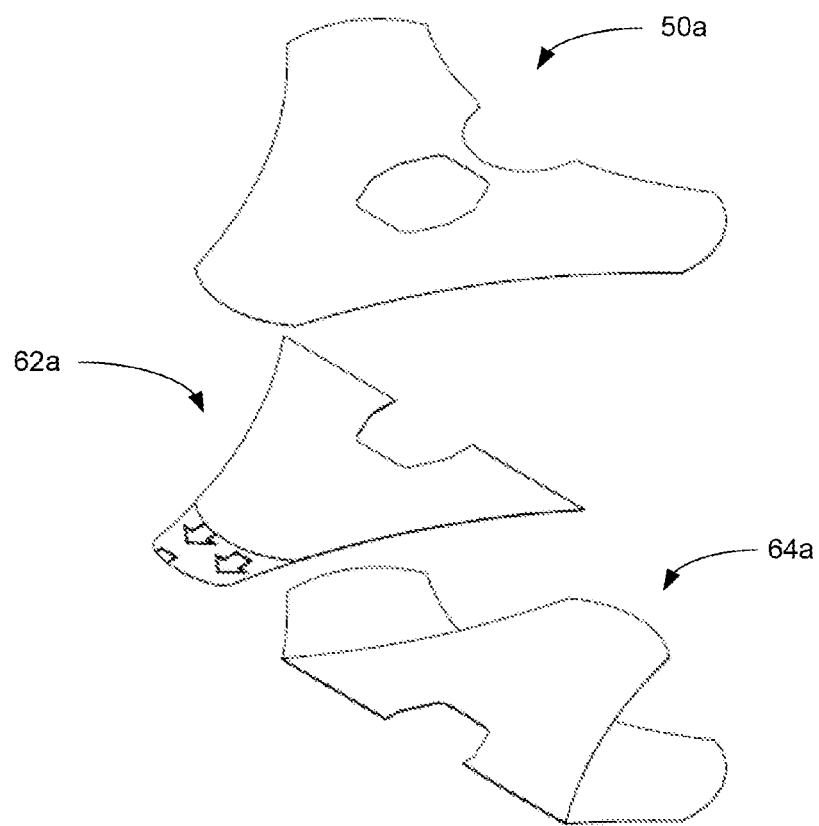
Figure 12F:
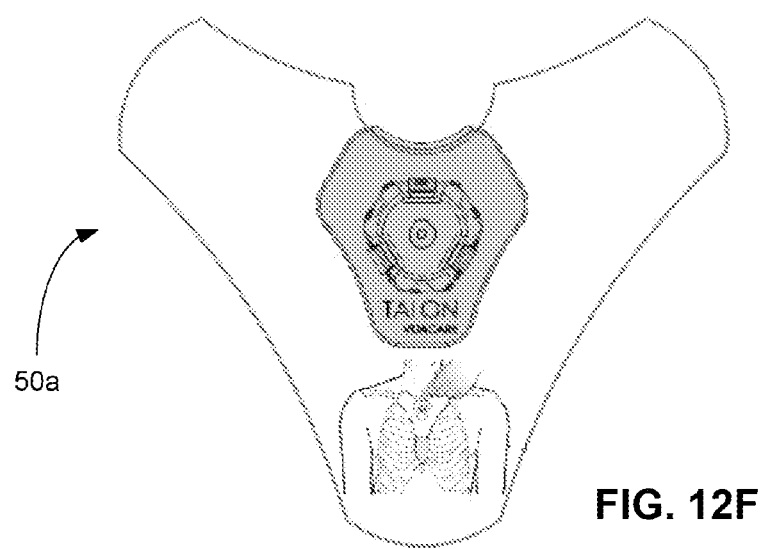
Figure 12G:
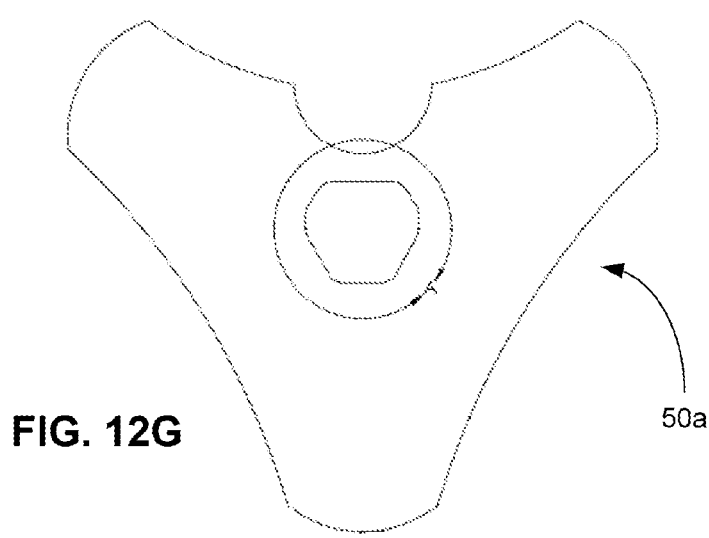
Figure 12H:
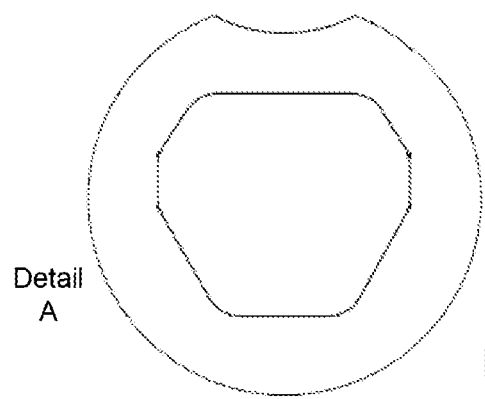
Figure 12I:
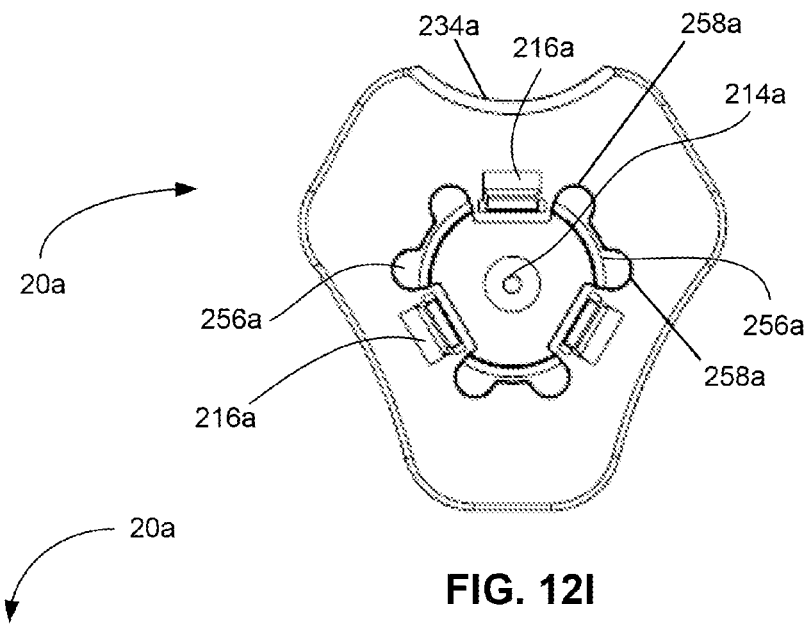
FIGS. 12I-12N depict various views of another embodiment of the present stabilizers shown with probes and for use in at least some embodiments of the present sternal locators, such as, for example, as shown in the sternal locator of FIGS. 12A-12C.
Figure 12J:
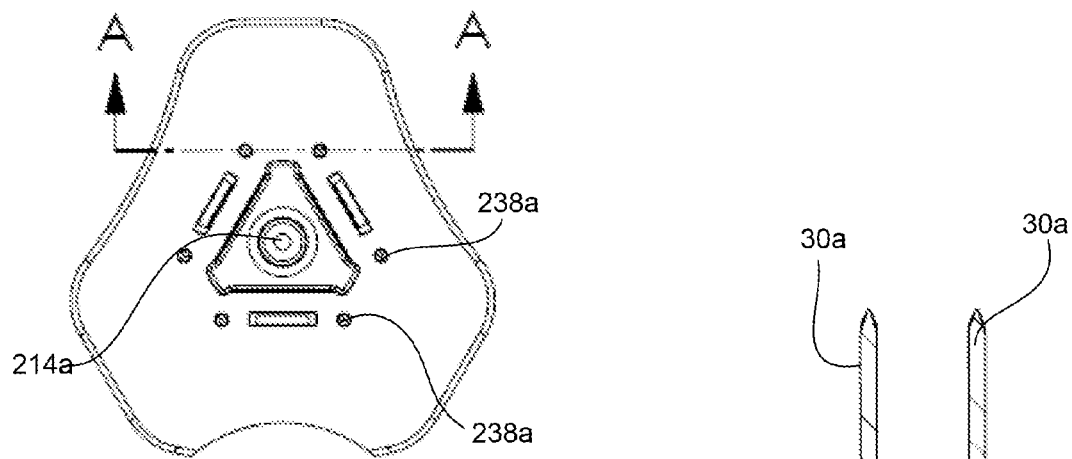
Figure 12K:
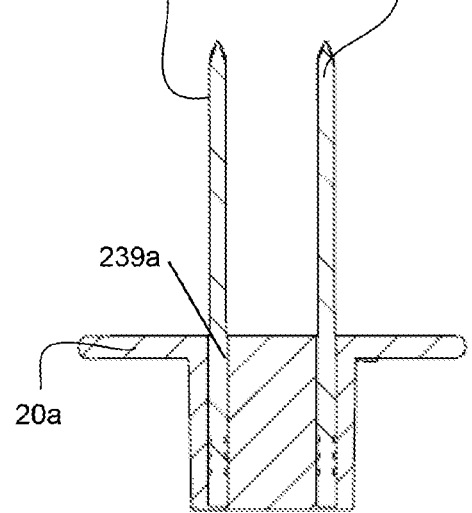
Figure 12L:
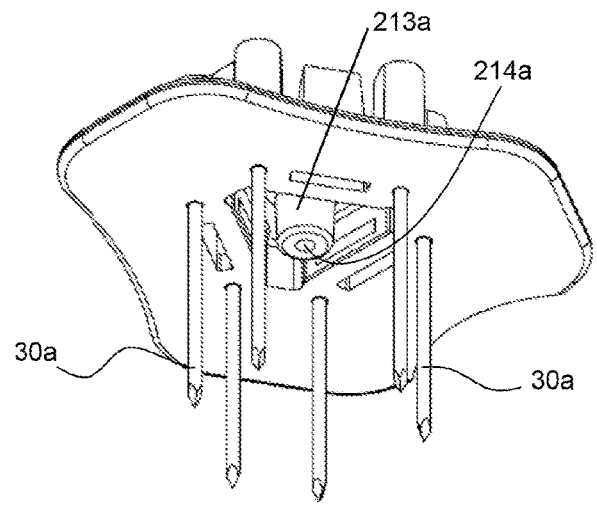
Figure 12M:
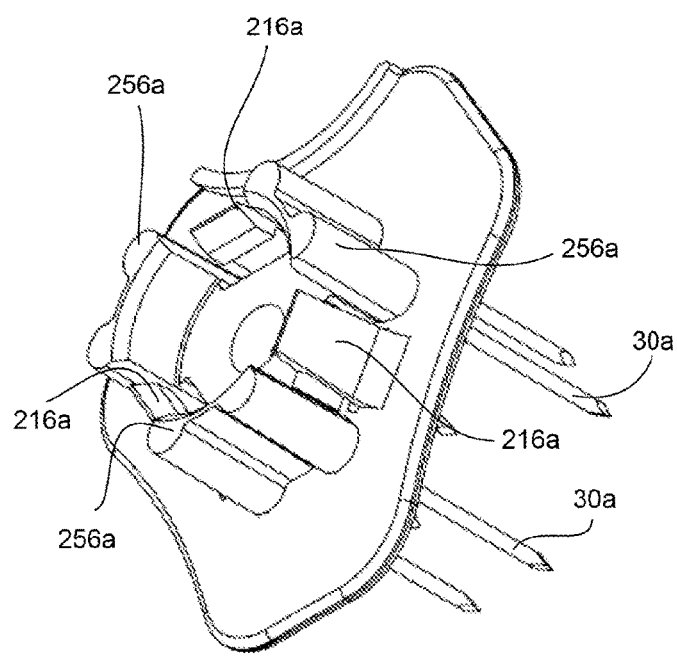
Figure 12N:
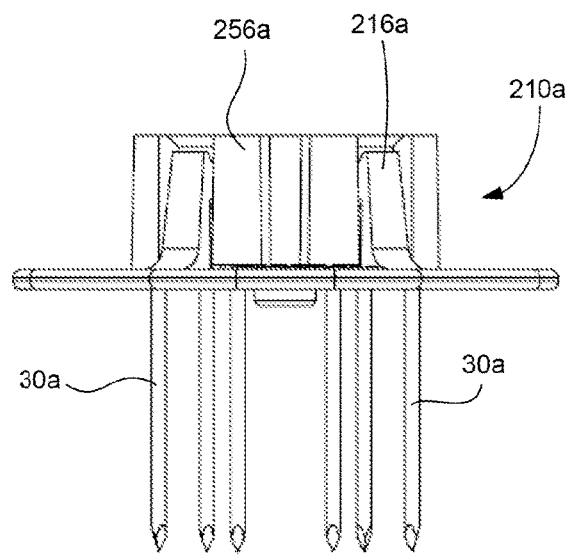

FIGS. 12A-12N depict various views of a second embodiment 10a of the present sternal locators and various components. Sternal locator 10a is similar in many respects to sternal locator 10, described above. For example, sternal locator 10a comprises stabilizer 20a (which is also similar in many respects to stabilizer 20), a flange portion of which is located between and coupled to a top sheet 40a (similar to top sheet 40) and an adhesive member 50a (similar to adhesive member 50). And as with top sheet 40 and adhesive member 50, top sheet 40a and adhesive member 50a are coupled to each other in this embodiment. Similarly, sternal locator 10a is configured to be placed on the chest of a subject (e.g., a human patient) at a location near sternum 114 and aligned with sternal notch 104. Sternal locator 10a is also configured to ensure proper placement of an IO device in intraosseous space 116.

Collar 210a is, and more specifically the one or more tabs 216a of collar 210a are, configured to couple (e.g., secure) stabilizer 20a to an IO device. In the embodiment shown, tabs 216a are similar to tabs 216 of collar 210. As described above for tabs 216, the rigidity of tabs 216a serves to stabilize the IO device to which the sternal locator is coupled, both by resisting any outward longitudinal movement of the IO device (meaning movement out of the intraosseous space along the direction of insertion) as well as any movement that would otherwise result from the IO device canting from side-to-side or otherwise moving laterally. As with collar 210, collar 210a also includes longitudinally-oriented elements 256a that are similar to elements 256. For example, elements 256a are taller than tabs 216a and function to guide the IO device to the proper location as it enters the space bounded by collar 210a, which also helps to prevent damage to tabs 216a, and they help to resist any lateral pitching or movement of the IO device. Each element 256a includes a pair of longitudinally-oriented ribs 258a on opposing sides of the element that serve to increase the rigidity (and tendency to resist lateral bending) of element 256a, the ribs each being hollow to receive and surround a portion of a probe 30a. In the illustrated embodiment, alignment feature (or notch) 234a of stabilizer 20a is an arc-shaped portion of flange 230a, which is similar to alignment feature 234.

Stabilizer 20a primarily differs from stabilizer 20 in that stabilizer 20a comprises six openings 238a in underside 236a. A recess 239a extends from each opening 238a and is configured to receive a probe 30a, as illustrated in FIG. 12K. Other embodiments may comprise more or fewer recesses (and associated openings) configured to receive more or fewer probes 30a.

Figure 13A:
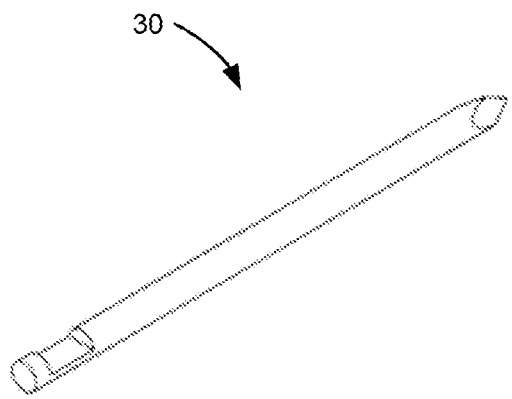
FIGS. 13A-13B depict one embodiment of the present probes for use with at least some embodiments of the present stabilizers, such as, for example, with the stabilizer of FIG. 8A.
Figure 13B:
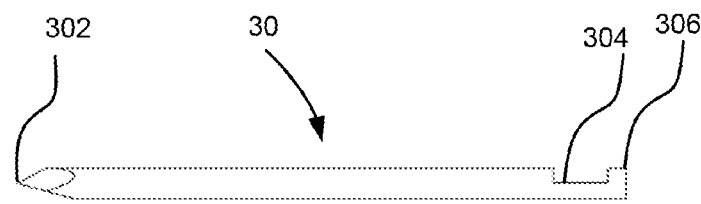

FIGS. 13A-13B depict a first embodiment 30 of the present probes that are suitable for use in at least some embodiments of the present sternal locators (e.g., sternal locator 10). In the embodiment shown, probe 30 comprises a pointed tip 302, a notch 304, and a proximal end 306, where notch 304 is closer to proximal end 306 than to tip 302. In certain embodiments, probes 30 comprise stainless steel, though other suitable sterile materials (or materials capable of being made sterile before use on a patient) may be used. Proximal end 306 is configured to be inserted into hole 238 and recess 239 of stabilizer 20. In some embodiments, probes 30 are fixed to stabilizer 20, such as by being bonded to stabilizer 20 using UV-curable adhesive applied to recess 239 and/or notch 304 and/or proximal end 306 of probe 30. In other embodiments, probe 30 may be force fit to hole 238 and recess 239 such that it is held in place by friction between the probe and the material of the stabilizer against which it is in contact. In still other embodiments, probes 30 may be fixed to stabilizer 20 as part of an injection molding process or using epoxy. Probe 30 can comprise any of various lengths and can extend, for example, 19-24 millimeters from a proximal-facing surface adjacent a passageway (e.g., from collar contact surface 212).

Figure 14A:
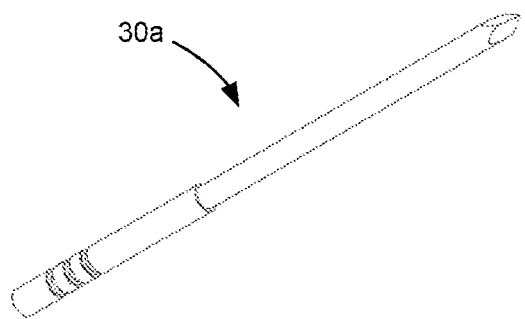
FIGS. 14A-14B depict another embodiment of the present probes for use with at least some embodiments of the present stabilizers, such as, for example, with the stabilizer of FIG. 12I.
Figure 14B:
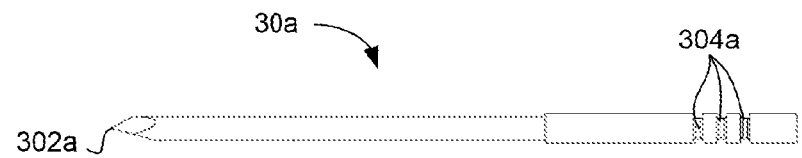

FIGS. 14A-14B depict a second embodiment 30a of the present probes that are suitable for use in at least some embodiments of the present sternal locators (e.g., sternal locator 10a). In the embodiment shown, probe 30a comprises a pointed tip 302a, a plurality of circumferential notches 304a, and a proximal end 306a, where notches 304a are closer to proximal end 306a than to tip 302a. In certain embodiments, probes 30a comprise stainless steel, though other suitable sterile materials (or materials capable of being made sterile before use on a patient) may be used. Proximal end 306a is configured to be inserted into hole 238a and recess 239a of stabilizer 20a. In some embodiments, probes 30a are fixed to stabilizer 20a, such as by being bonded to stabilizer 20a using UV-curable adhesive applied to recess 239a and/or notches 304a and/or proximal end 306a of probe 30a. In other embodiments, probe 30a may be force fit to hole 238a and recess 239a such that it is held in place by friction between the probe and the material of the stabilizer against which it is in contact. In still other embodiments, probes 30a may be fixed to stabilizer 20a as part of an injection molding process or using epoxy. Probe 30a can comprise any of various lengths and can extend, for example, 19-24 millimeters from a proximal-facing surface adjacent a passageway (e.g., from collar contact surface 212a).

Figure 15A:
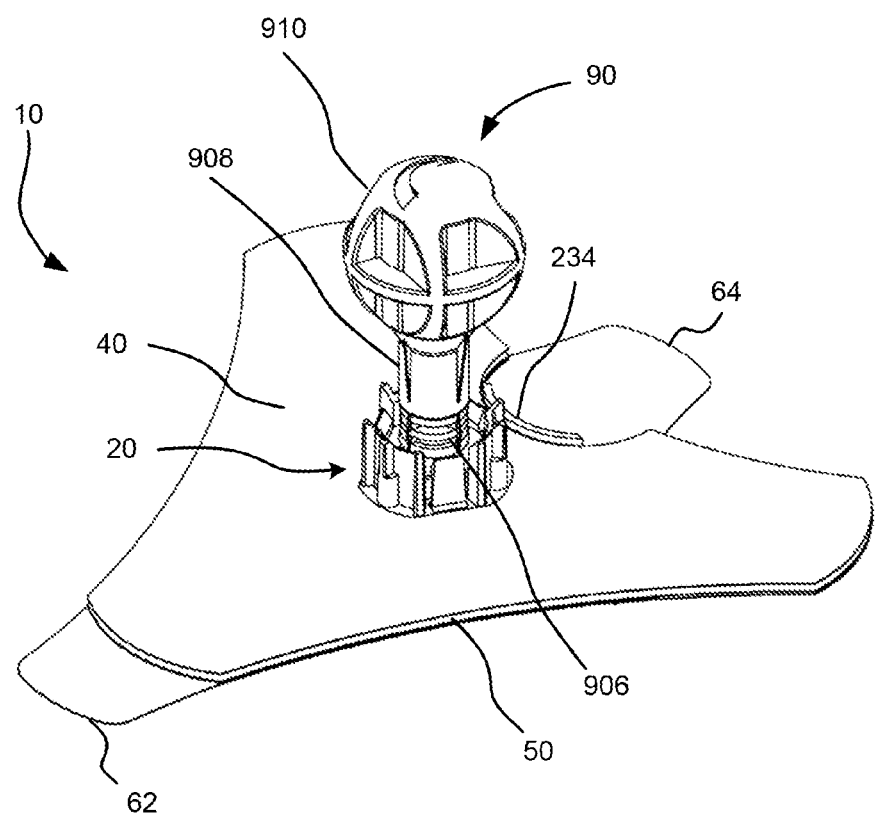
FIG. 15A is a perspective view of the IO device of FIG. 3A coupled to a sternal locator.
Figure 15B:
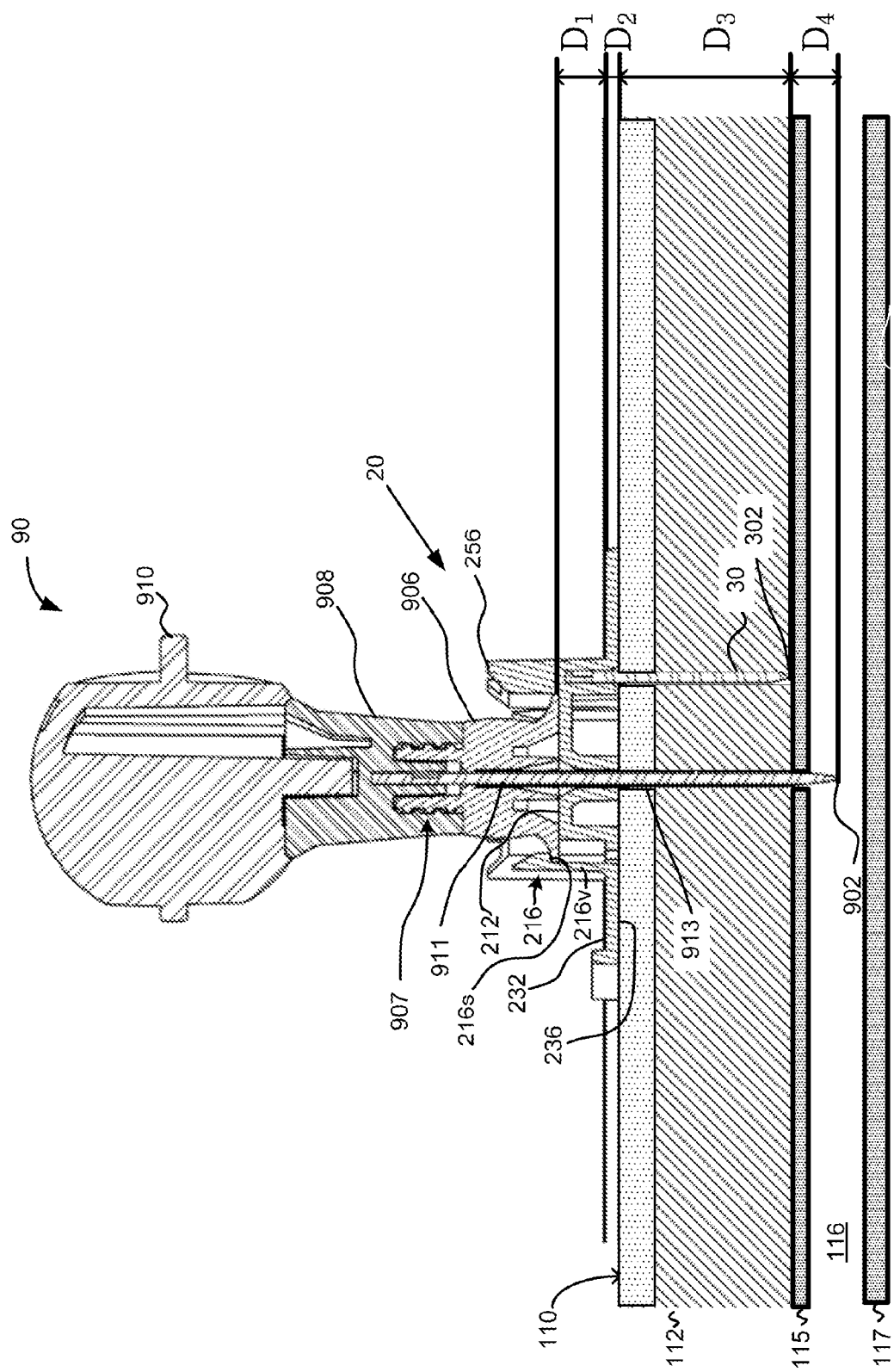
FIG. 15B shows the assembly of FIG. 15A in cross section and in use with a human subject.
Figure 15C:
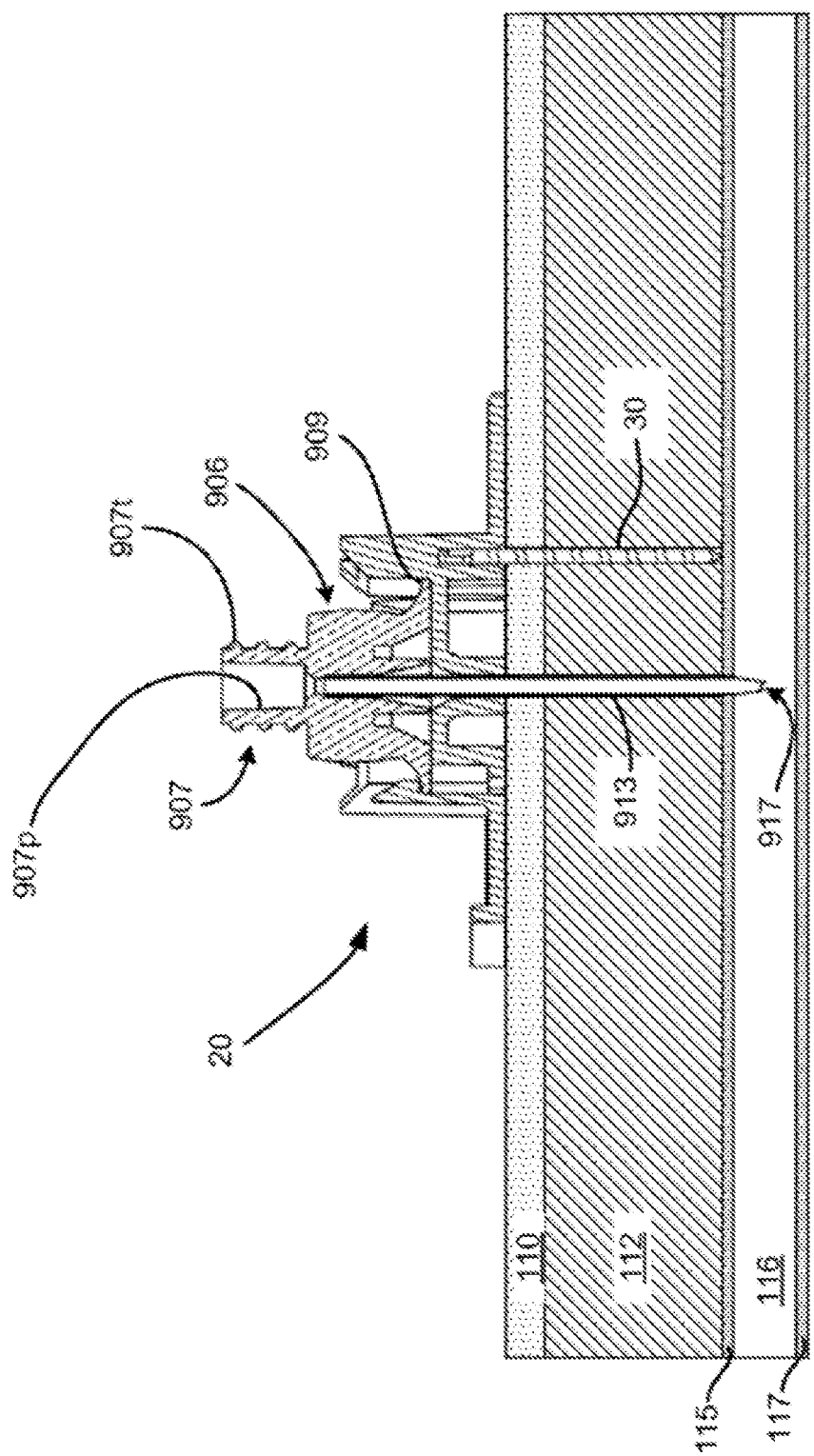
FIG. 15C depicts a cross-sectional view of the outer penetrator and associated hub of an IO device following its insertion into an IO space in the sternum and ready to be attached to a fluid source.

Methods of using of embodiments of the present sternal locators 10 and 10a (e.g., as illustrated and described with reference to sternal locator 10, but similar for at least some embodiments of sternal locator 10a) to locate a preferred location for IO device 90 to be inserted (e.g., driven) into the sternum of a patient will now be discussed. FIG. 15A depicts a perspective view of sternal locator 10 coupled to IO device 90, while FIG. 15A depicts a cross-sectional view of IO device 90 coupled to sternal locator 10 in use on a human patient (adhesive member 50 and top layer 40 have been omitted for clarity). Four dimensions are shown in FIG. 15A. $D_1$ is the distance from collar contact surface 212 to top surface 232 of flange 230. $D_2$ includes the thickness of the flange and any adhesive on the underside of underside 236 or any adhesive member 50 (not shown). $D_3$ is the distance from the lower of underside 236 or any adhesive or adhesive member attached to underside 236 to tip 302 of probe 30. $D_4$ is the distance from probe tip 302 to tip 902 of inner penetrator 911. Therefore, the overall exposed length of inner penetrator 911 (the portion of inner penetrator 911 that extends beyond hub 906) is $D_1+D_2+D_3+D_4$.

In the illustrated embodiment, $D_1$ is about 5.25 mm, $D_2$ is about 2.0 mm, $D_3$ is about 23.5 mm, and $D_4$ is about 7.75 mm; therefore, about 38.5 mm of inner penetrator 911 is exposed or protrudes beyond inner penetrator hub 906. About 23.5 mm of probes 30 is exposed or protrudes beyond underside 236 of stabilizer 20. In some embodiments, inner penetrator 911 may protrude about 1.5 mm beyond outer penetrator 913. When IO device 90 is coupled to sternal locator 10 such that tabs 216 are in a "locked" position (and surfaces 216s bear against the upper surface of the flanged portion of distal end 909 of hub 906), inner penetrator 911 extends about 7.0 to 8.0 mm beyond probes 30. Depending on the application, the exposed portions of inner penetrator 911 and probes 30 may be lesser or greater than what is shown and described. For example, inner penetrator 911 and probes 30 may be shorter when the sternal locator and IO device are intended for use on infants or children (and inner penetrator 911 may extend a shorter distance beyond probes 30). In other embodiments, inner penetrator 911 and probes 30 may be longer (and inner penetrator 911 may extend a greater distance beyond probes 30) when the sternal locator and IO device are intended for use on obese patients, large patients, or patients with a thicker than normal sternum. In other embodiments, $D_1$ may be about 5.25 mm, $D_2$ may be about 1.25 mm, $D_3$ may be about 23.5 mm, and $D_4$ may be about 6.0 mm; such that about 32 mm of inner penetrator 911 is exposed or protrudes beyond inner penetrator hub 906 and/or about 19.5 mm of probes 30 protrudes beyond underside 236 of stabilizer 20. Any dimension listed as "about" may also be substantially (including exactly) equal to the given value.

To use sternal locator 10, a user first locates sternal notch 104 of the patient by feeling for the U-shaped cavity above the sternum, below the throat, and between the clavicles. The user then aligns alignment feature 234 of sternal locator 10 with sternal notch 104, ensuring that the balance of the sternal locator is positioned over the patient's sternum. With sternal locator 10 thus properly aligned, the user then applies pressure to sternal locator 10 until probes 30 penetrate skin 110 and muscle 112 and touch anterior compact bone 115 (the top surface of the sternum). Probes 30 may penetrate into anterior compact bone 115 by some distance, such as about 0.5 mm to about 1.0 mm (which accounts for the difference between the illustrative 7.0 mm length that inner penetrator 911 extends beyond probes 30 and the illustrative value of 7.75 mm for D4), though preferably penetrate no more than 0.5 mm, and in no case should probes 30 penetrate into intraosseous space 116. The user then removes removable liners 62, 64 and presses adhesive member 50 against skin 110, ensuring that adhesive member 50 is adhered to skin 110 of the patient.

In the illustrated embodiment, the thickness of skin 110 and subcutaneous tissue 112 are equal in thickness to $D_3$, the exposed length of probes 30. However, the thickness of skin 110 and subcutaneous tissue 112 can vary widely depending on the patient. Thus, in some patients, length of probes 30 will exceed the tissue thickness such that stabilizer 20 is not flush with skin 110 and portions of probes 30 are exposed. In such instances, adhesive layer 50 provides an additional stabilizing effect by allowing sternal locator 10 to be affixed to the patient's chest.

Once sternal locator 10 has been properly affixed to the patient's chest, the user then introduces the distal portion of IO device 90 (which includes portions of outer penetrator 913 and driver 901) into passageway 214 of sternal locator 10. The user applies pressure and twists or reciprocates IO device 90 (back and forth, but not necessarily all the way around, such that the driving movement may be characterized as reciprocating, twisting, or non-rotational (meaning one complete revolution is not utilized)) until inner penetrator 911 and outer penetrator 913 pierce skin 110, subcutaneous tissue 112, and anterior compact bone 115. IO device 90 is properly positioned when surfaces 216s of tabs 216 fully engage (or are in contact with) the flanged portion of distal end 909 of hub 906. In certain embodiments, an audible sound (e.g., a click) may be heard as tabs 216 pass over the flanged portion of distal end 909 of inner penetrator hub 906 and snap into place. Furthermore, the user will feel the IO device passing tabs 216 because the force required to advance the device will be reduced (thus, the user will feel the IO device "snap" into place). Introducing IO device 90 into the patient in this manner may be described as non-surgically introducing (or inserting) the IO device, or introducing (or inserting) the IO device without first making an incision for the IO device with a different structure (such as a scalpel). When stabilizer 20 is sized as shown in the figures, the force that is required to drive the IO device shown in the figures into engagement with the depicted stabilizer is greater than the force that will be required to drive the stabilizer through the skin and subcutaneous tissue and into contact with anterior compact bone 215 in most patients.

Driver 901 may then be removed from IO device 90 by, in the depicted embodiment, rotating grip 910 in a counter-clockwise direction to uncouple inner penetrator hub 908 from outer penetrator hub 906. This will withdraw inner penetrator 911 from outer penetrator 913. Depending on the type of IO device used, the removal of the inner penetrator may differ. Furthermore, some embodiments of IO devices may include a closed-tip needle with a side port located sufficiently close to the distal-most end of the closed-tip needle for the intended IO application, such that no inner penetrator 911 is used.

Outer penetrator 913 remains coupled to stabilizer 20 of sternal locator 10. A conduit is thus formed from open, proximal end 907 of outer penetrator hub 906 through distal opening 917 of outer penetrator 913, which is in direct fluid communication with intraosseous space 116, as shown in FIG. 5B. A fluid source may then be coupled to proximal end 907 of outer penetrator hub 906 for delivery of fluid (e.g., blood or medicine) to intraosseous space 116.

Figure 17A:
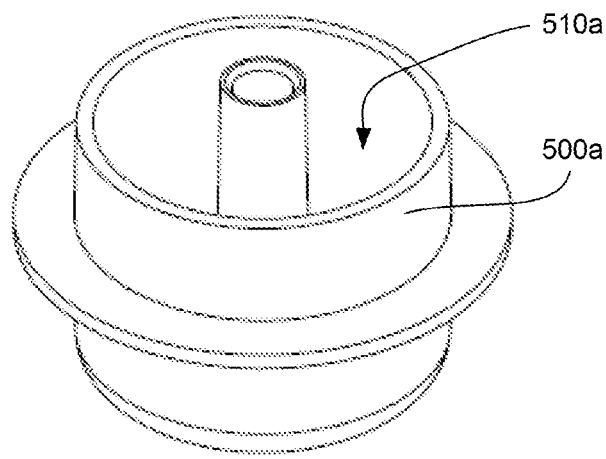
FIGS. 17A-17D depict various views of another embodiment of the present open containers.
Figure 17B:
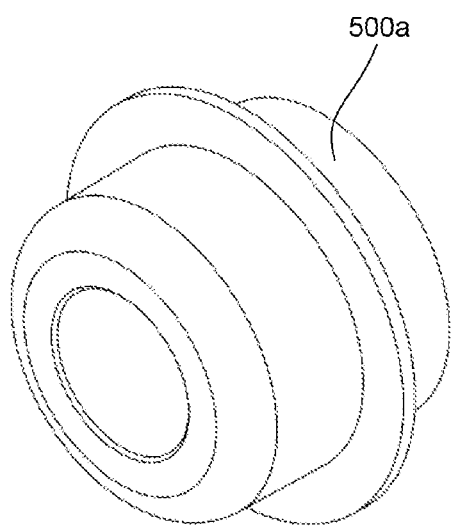
Figure 17C:
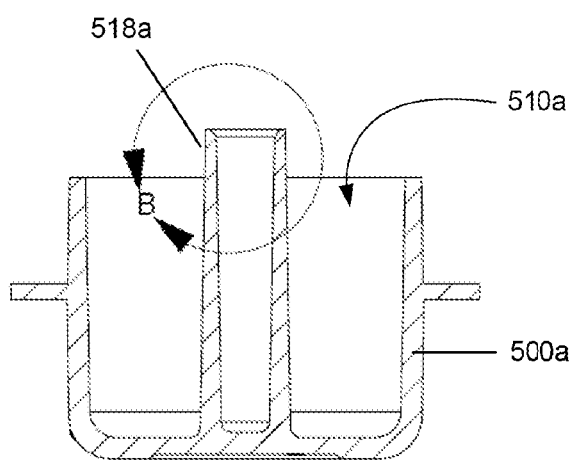
Figure 17D:
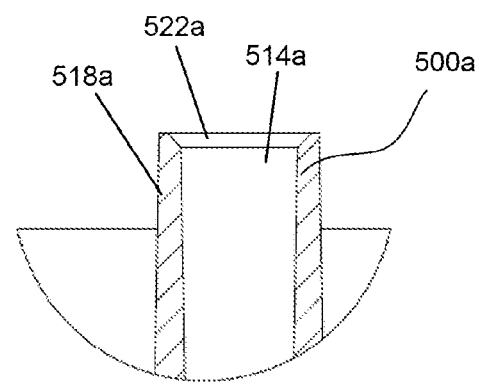
Figure 17E:
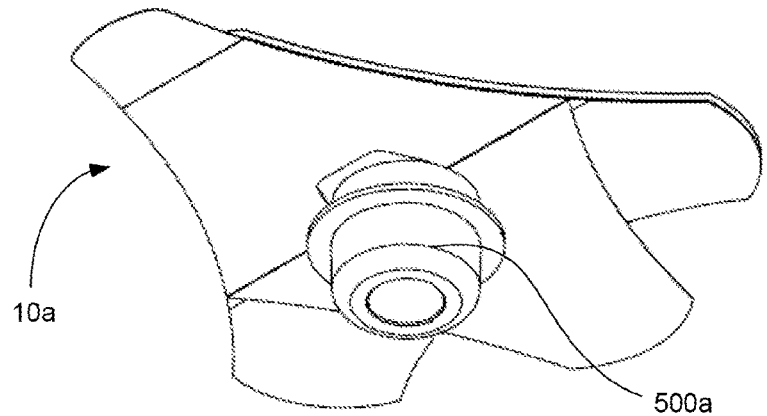
FIGS. 17E-17G depict the open container of FIG. 17A coupled to the sternal locator of FIG. 6.
Figure 17F:
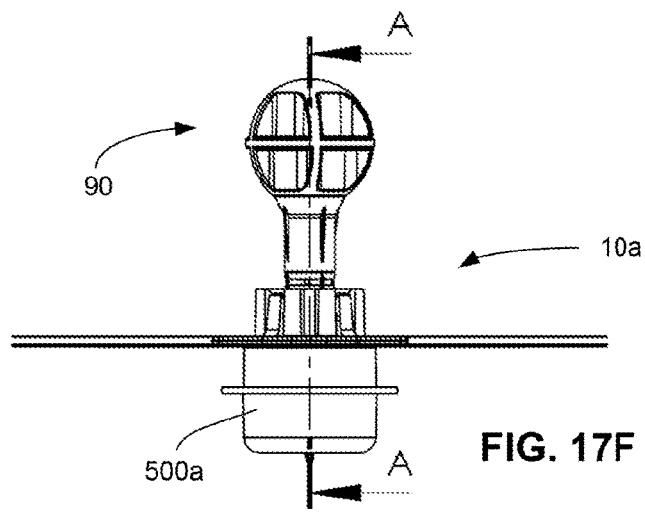
Figure 17G:
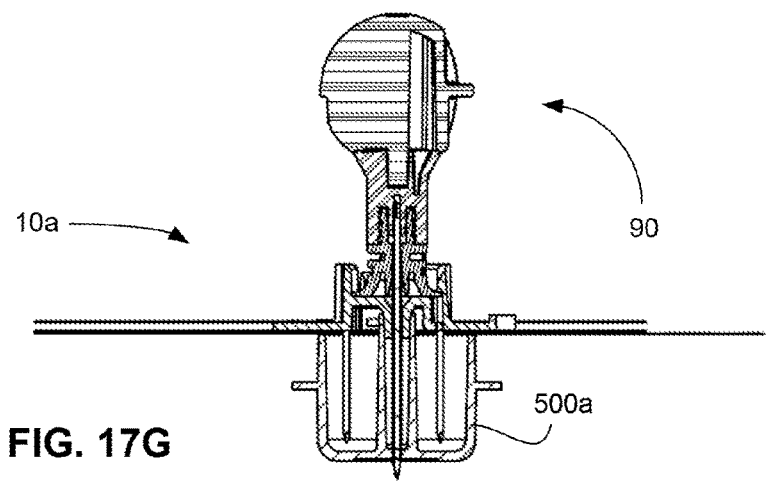

After use, the sternal locator and IO device may be withdrawn from the patient's chest, and the probes and penetrator of the IO device may be inserted into penetrable material 400 (see FIG. 16C), which may be disposed in some embodiments in a reservoir (e.g., reservoir 510 of open container 500 as depicted in FIGS. 16A-16C, reservoir 510a of open container 500a as depicted in FIGS. 17A-17D, or the like). Together, open container 500 and penetrable material 400 may be used as a sharps container for the assembly comprising the sternal locator and the IO device. Penetrable material 400 may be held to open container 500 through an adhesive member (not visible), a friction fit, or through any other suitable means. Other embodiments, such as open container 500a of FIGS. 17A-17D, may not include penetrable material, and may instead include an opening 514a configured to receive and engage protrusion 213 or 213a of stabilizer 20 or 20a, respectively (shown in FIGS. 17E-17F engaged with 213a of stabilizer 20a of sternal locator 10a) to couple hollow container 500a to the sternal locator to cover the probes and penetrators of the sternal locators. For example, in the embodiment shown, hollow container comprises a central, hollow stem 518a with opening 514a defined in a proximal end of the stem, as shown. In the embodiment shown, central stem 518a further includes a proximal surface 522a tapering the proximal end of opening 514a to facilitate insertion of protrusion 213a into opening 514a.

Some embodiments of the present systems (which may be termed kits) may include a package (e.g., a flexible package (e.g., such as one that does not include a tray, such as a rigid plastic tray)) that contains at least one of the present sternal locators, one of the present sharps containers, and, in more specific embodiments, one of the disclosed IO devices and/or instructions for use, which instructions may be on the outside of the package, on the sternal locator, and/or on an insert contained within the package.

Figure 18B:
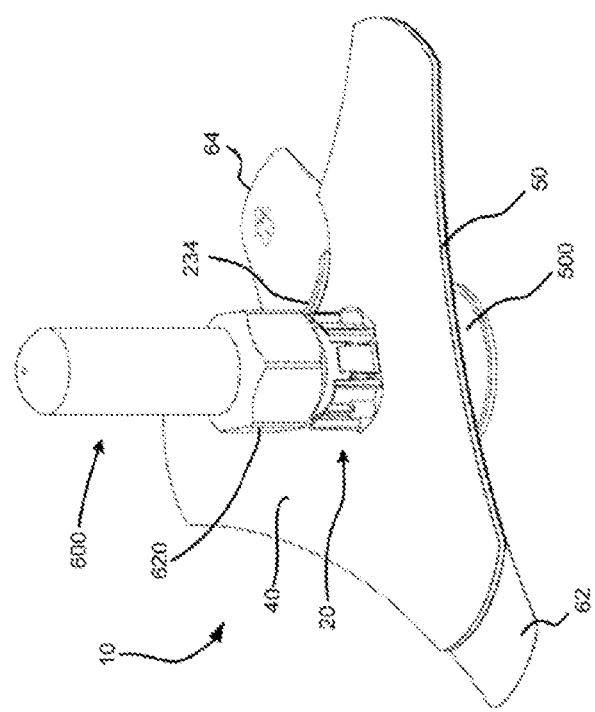
FIG. 18B is a perspective view of the removal tool shown of FIG. 18A coupled to the outer penetrator hub of IO device of FIG. 3A in use with the sternal locator of FIG. 6.
Figure 18A:
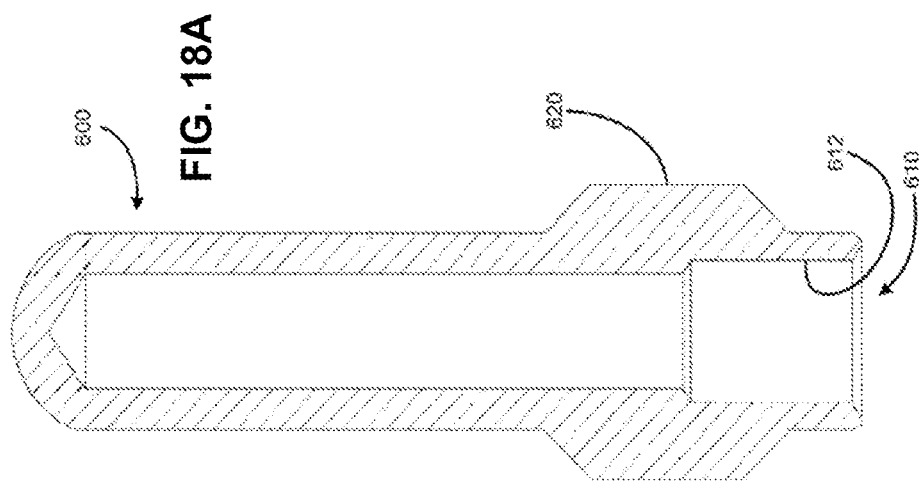
FIG. 18A is a cross-sectional view of one of the present removal tools.
Figure 19A:
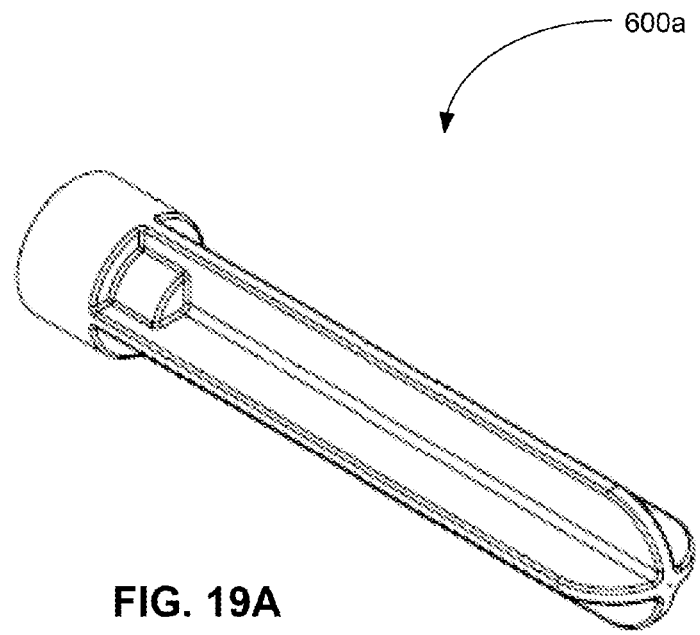
FIGS. 19A-19D depict various views of another embodiment of the present removal tools.
Figure 19B:
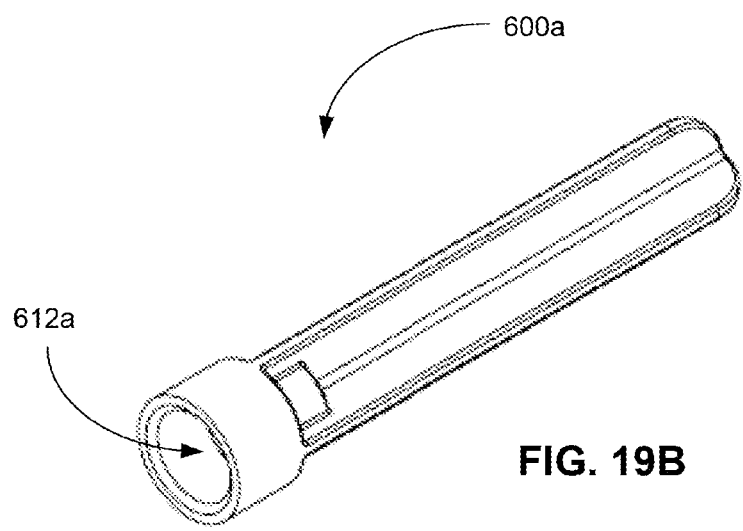
Figure 19C:
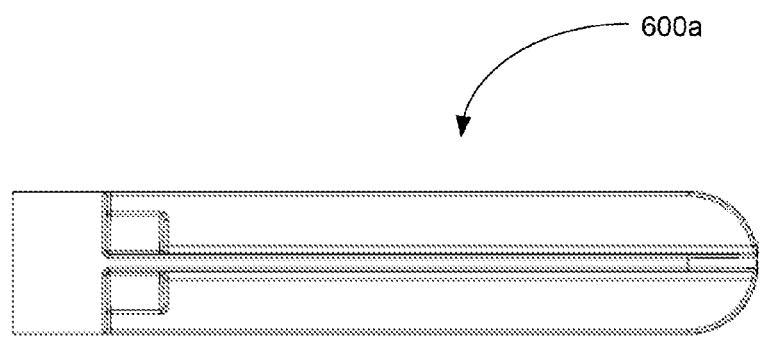
Figure 19D:
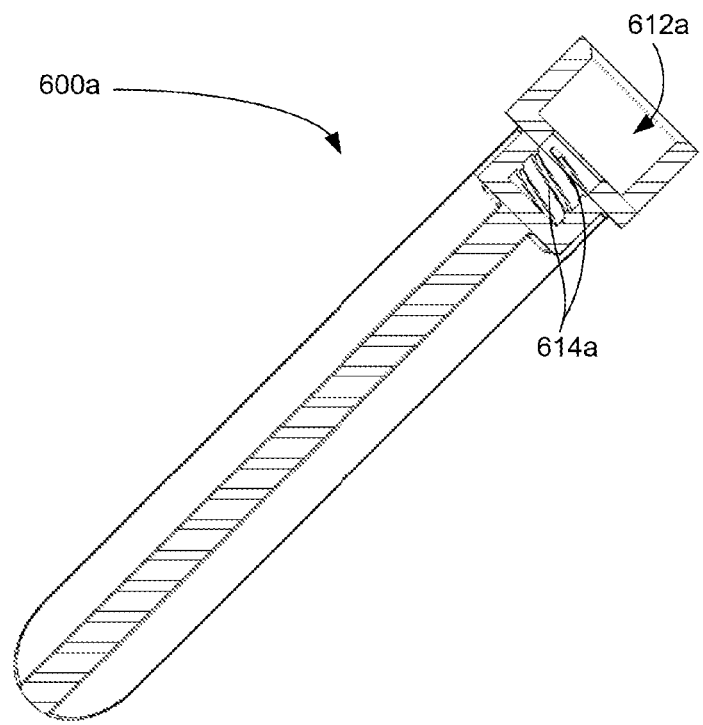

Some embodiments of the present methods are training methods, and include placing sternal locator 10 into penetrable material 400, then inserting at least the outer penetrator of IO device 90 (and, in some embodiments, all of IO device 90) into collar 210 of stabilizer 20 until stabilizer 20 is engaged with IO device 90 (as described above). The release liners may be removed or left in place as part of the training method. IO device 90 may then be removed from engagement with the sternal locator using one of the present removal tools, such as removal tool 600 shown in FIGS. 18A and 18B, or removal tool 600a depicted in FIGS. 19A-19D. Removal tool 600 includes open distal end 610 that includes recess 612, which is sized to receive outer penetrator hub 906, and an enlarged gripping section 620. Depending on the depth of penetrable material 400, a user may press and hold the sternal locator and the outer penetrator into container 500 such that the distal end of the outer penetrator contacts the bottom of reservoir 510 and the top surface of the flange of outer penetrator hub 906 contacts surfaces 216s of tabs 216. A user may then slide or twist removal tool 600 over outer penetrator hub 906 and press the tool against tabs 216 with enough force to the inwardly-projecting portions 216i of the tabs. For example, a removal tool (e.g., removal tool 600a) can include a recess 612a with threads 614a (e.g., female threads) configured to be coupled to outer penetrator hub 906 (e.g., via complimentary male threads). A user may continue pushing on or twisting the removal tool, which will push the stabilizer downward relative to the outer penetrator because the prongs of the stabilizer will not have reached the bottom of the reservoir while the outer penetrator, in contrast, will be in contact with the bottom of the reservoir, such that at least a portion of the tabs of the stabilizer move sufficiently distal past the flange of the distal end of the outer penetrator hub that the outer penetrator can be removed. A user can then remove the removal tool and the outer penetrator (e.g., simultaneously). While movement of the outer penetrator can be impeded by the bottom of the reservoir of the container (which is a type of sharps container), any surface or technique for allowing the removal tool to push the stabilizer distal relative to the outer penetrator can be used to disengage the outer penetrator from the stabilizer (e.g., a user may contact the distal end of the outer penetrator against any suitable surface that will impede distal movement of the outer penetrator as the tab or tabs of the stabilizer are spread apart and the stabilizer pushed distally relative to the outer penetrator).

Non-limiting examples of suitable materials for some embodiments of the present stabilizers, the present grips, and the present hubs of the disclosed IO devices include injection moldable plastics, such as Bayer RX2530 polycarbonate (USP grade VI, gamma stable). A non-limiting example of a suitable material for some embodiments of the present probes is stainless steel, such as 304V stainless steel straightened wire that is spring tempered in accordance with ASTM-A313 with tensile strength of 265 to 293 PSI. A non-limiting example of a suitable material for some embodiments of the present open containers is medical grade plastic, such as white DELRIN. A non-limiting example of a suitable material for some embodiments of the present penetrable materials is ¾-inch thick white polyethylene foam with an adhesive backing member (McMaster-Carr P/N 8865K521).

It should be understood that the present devices and methods are not intended to be limited to the particular forms disclosed. Rather, they are to cover all modifications, equivalents, and alternatives falling within the scope of the claims. For example, other embodiments of the present sternal locators may include a single tab for engaging an IO device, or more tabs (and more probes) than the version of the stabilizer shown in the figures, such as four tabs and four probes. As another example, in some embodiments, top layer 40 may include a depiction of a portion of a subject's anatomy to help a user determine whether to place the sternal locator in use. As another example, the sternal locator may include a protective cover (comparable to removable cover 990 of IO device 90) coupled to the stabilizer prior to use to prevent probes 30 from sticking things inadvertently. As another example, the probe or probes that are used may comprise coring needles rather than solid material.

The claims are not to be interpreted as including means-plus- or step-plus-function limitations, unless such a limitation is explicitly recited in a given claim using the phrase(s) "means for" or "step for," respectively.

The invention claimed is:

1. A method for accessing bone marrow in a sternum of a human patient, comprising:
   locating a sternal notch on a chest of the patient;
   placing a sternal locator having an alignment feature on the chest of the patient such that the alignment feature is aligned with the sternal notch, the sternal locator including a stabilizer having one or more longitudinally-oriented flexible tabs having a longitudinal axis extending vertically from a first surface of the stabilizer and configured to secure the stabilizer to an intraosseous (IO) device, and two or more probes coupled to and extending from a second surface of the stabilizer;
   contacting the sternal locator directly with a gloved or ungloved hand of a user and pushing the sternal locator against the chest of the patient until the two or more probes penetrate skin of the patient and contact anterior compact bone of the patient's sternum;
   manually inserting an intraosseous (IO) device into the patient, the IO device comprising a penetrator having a tip, and a hub coupled to the penetrator, the hub comprising a flanged portion, where the manually inserting includes inserting the penetrator through a passageway in the sternal locator; and manually applying pressure to the IO device until all of the one or more longitudinally-oriented tabs engage the flanged portion of the hub.

2. The method of claim 1, where the sternal locator includes an underside, an adhesive member coupled to the underside, and at least one removable liner coupled to the adhesive member, the method further comprising prior to the inserting the IO device:
removing the at least one removable liner from the adhesive member.

3. The method of claim 2, the method including pressing the adhesive member against the skin of the patient.

4. The method of claim 1, further comprising delivering fluid through the IO device and into an intraosseous space in the sternum of the patient.

5. The method of claim 1, further comprising securing the stabilizer to the IO device after a portion of the IO device has been inserted into the patient.

6. The method of claim 1, wherein the stabilizer further comprises a circumferential collar comprising: a collar contact surface configured to contact a portion of the IO device, and a passageway configured to receive the penetrator of the IO device.

7. The method of claim 1, wherein the alignment feature is an arc-shaped surface.

8. The method of claim 1, wherein each of the one or more longitudinally-oriented tabs includes an inwardly-projecting portion.

9. The method of claim 1, wherein the two or more probes are fixed to the stabilizer.

10. The method of claim 1, wherein the two or more probes comprise stainless steel.

11. The method of claim 1, wherein the penetrator of the IO device includes an inner penetrator coupled to an outer penetrator, the outer penetrator having an open outer penetrator distal end, the inner penetrator having a tip, a portion of the inner penetrator is positioned in the outer penetrator, and the tip of the inner penetrator is distal of the open outer penetrator distal end.

12. The method of claim 11, wherein the IO device includes a grip coupled to an outer penetrator hub that is coupled to the outer penetrator.

13. The method of claim 12, wherein the grip is fixedly attached to the outer penetrator hub.

14. The method of claim 11, wherein the inner penetrator is coupled to an inner penetrator hub and the inner penetrator hub and outer penetrator hub are coupled to each other through complimentary Luer connectors.

15. A method for accessing bone marrow in a sternum of a human patient, the method comprising:
providing an intraosseous device comprising a penetrator coupled to a hub;
providing a sternal locator comprising an alignment feature and a stabilizer, the stabilizer including a tab having a longitudinal axis extending vertically from a first surface of the stabilizer and configured to secure the stabilizer to the intraosseous device, a probe extending from a second surface of the stabilizer, and a passageway extending through the stabilizer from the first surface to the second surface;
locating a sternal notch on a chest of the patient and placing the sternal locator on the chest of the patient such that the alignment feature is aligned with the sternal notch;
applying pressure to the sternal locator until the probe penetrates skin and touches anterior compact bone of the patient's sternum;
inserting the penetrator of the intraosseous device through the passageway of the stabilizer; and
applying pressure to the intraosseous device to pierce the skin and the anterior compact bone until the tab engages the hub of the penetrator.

16. The method according to claim 15, wherein the tab is configured to flex outwardly away from a center of the stabilizer as a portion of the tab contacts a portion of the hub while inserting the penetrator of the intraosseous device through the passageway of the stabilizer.

17. The method according to claim 16, wherein passing the portion of the hub of the penetrator over the portion of the tab results in an audible sound indicating the tab has snapped into place.

18. The method according to claim 16, wherein passing the portion of the hub of the penetrator over the portion of the tab results in a tactile feedback indicating the tab has snapped into place.

19. A method for accessing bone marrow in a sternum of a human patient, the method comprising:
providing an intraosseous device comprising an outer penetrator coupled to an outer penetrator hub, and an inner penetrator coupled to an inner penetrator hub, the outer penetrator configured to slidably receive a portion of the inner penetrator;
providing a sternal locator comprising an alignment feature and a stabilizer, the stabilizer including a flexible tab having a longitudinal axis extending vertically from a first surface of the stabilizer and configured to secure the stabilizer to the intraosseous device, a probe extending from a second surface of the stabilizer, and a passageway extending through the stabilizer;
locating a sternal notch on a chest of the patient and placing the sternal locator on the chest of the patient such that the alignment feature is aligned with the sternal notch;
applying pressure to the sternal locator until the probe penetrates skin and touches anterior compact bone of the patient's sternum;
inserting the intraosseous device through the passageway of the stabilizer and applying pressure to the intraosseous device to pierce the skin and the anterior compact bone until the tab engages the outer penetrator hub; and
withdrawing the inner penetrator from the outer penetrator such that the outer penetrator remains coupled to the stabilizer of the sternal locator to form a conduit in direct fluid communication with an intraosseous space.

20. The method according to claim 19, wherein a surface of the flexible tab is configured to resist or impede travel of the outer penetrator after the outer penetrator is inserted in the intraosseous space.

* * * * *